US010179805B2

(12) United States Patent
Ross et al.

(10) Patent No.: US 10,179,805 B2
(45) Date of Patent: Jan. 15, 2019

(54) COMPUTATIONALLY OPTIMIZED BROADLY REACTIVE ANTIGENS FOR HUMAN AND AVIAN H5N1 INFLUENZA

(71) Applicant: University of Pittsburgh-Of the Commonwealth System of Higher Education, Pittsburgh, PA (US)

(72) Inventors: Ted M. Ross, Athens, GA (US); Corey J. Crevar, North Huntingdon, PA (US); Brendan M. Giles, Denver, CO (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/391,554

(22) Filed: Dec. 27, 2016

(65) Prior Publication Data
US 2017/0107262 A1 Apr. 20, 2017

Related U.S. Application Data

(62) Division of application No. 14/377,633, filed as application No. PCT/US2013/025284 on Feb. 8, 2013, now Pat. No. 9,566,327.

(60) Provisional application No. 61/597,998, filed on Feb. 13, 2012.

(51) Int. Cl.
| *C07K 14/11* | (2006.01) |
| *C07K 14/005* | (2006.01) |
| *A61K 39/12* | (2006.01) |
| *A61K 39/145* | (2006.01) |
| *C12N 5/071* | (2010.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *A61K 39/145* (2013.01); *C12N 5/0686* (2013.01); *C12N 7/00* (2013.01); *A61K 2039/5258* (2013.01); *A61K 2039/55505* (2013.01); *A61K 2039/55561* (2013.01); *A61K 2039/575* (2013.01); *C07K 2319/00* (2013.01); *C12N 2760/16034* (2013.01); *C12N 2760/16122* (2013.01); *C12N 2760/16123* (2013.01); *C12N 2760/16134* (2013.01); *C12N 2760/16171* (2013.01); *C12N 2760/16222* (2013.01); *C12N 2760/16234* (2013.01)

(58) Field of Classification Search
CPC .......... C07K 14/14; C12N 2720/12323; C12N 2770/32122; A61K 2039/5258
See application file for complete search history.

(56) References Cited

U.S. PATENT DOCUMENTS

| 7,566,454 B2 | 7/2009 | Lu et al. |
| 2005/0181459 A1 | 8/2005 | Baker et al. |
| 2008/0045472 A1 | 2/2008 | Brahmachari et al. |
| 2009/0074803 A1 | 3/2009 | Sallberg et al. |
| 2009/0291472 A1 | 11/2009 | Lu et al. |
| 2009/0327170 A1 | 12/2009 | Donati et al. |
| 2010/0041740 A1 | 2/2010 | Wong et al. |

FOREIGN PATENT DOCUMENTS

| CN | 1772887 A | 5/2006 |
| WO | WO 2008/028946 | 3/2008 |
| WO | WO 2009/073330 | 6/2009 |
| WO | WO 2010/036948 | 4/2010 |
| WO | WO 2010/036970 | 4/2010 |
| WO | WO 2010/115133 | 10/2010 |
| WO | WO 2011/094358 | 8/2011 |
| WO | WO 2012/036993 | 3/2012 |
| WO | WO 2012/177760 | 12/2012 |
| WO | WO 2013/119683 | 8/2013 |

OTHER PUBLICATIONS

Guan Y et al. Proc. Nat. Acad. Sci. USA, 2004, vol. 101 (21), pp. 8156-8161.*
Beckman Coulter, "Codon Optimization to PCR," *Nature*, vol. 425:540, 2003.
Butt et al., "Avian Influenza A (H9N2): A Computational Molecular Analysis and Phylogenetic Characterization of Viral Surface Proteins Isolated Between 1997 and 2009 from the Human Population," *Virol. J.*, vol. 7:319-330, 2010.
Cal et al., "A Computational Framework for Influenza Antigenic Cartography," *PLoS Comput. Biol.*, vol. 6:e1000949, 2010.
Carter et al., "Complex Patterns of Human Antisera Reactivity to Novel 2009 H1N1 and Historical H1N1 Influenza Strains," *PLoS One* 7(7):e39435, 2012.
Chen et al., "Establishment of multiple sublineages of H5N1 influenza virus in Asia: Implications for pandemic control," *Proc Natl Acad Sci USA* 103(8):2845-2850, 2006.
Chen et al., "A consensus-hemagglutinin-based DNA vaccine that protects mice against divergent H5N1 influenza viruses," *Proc Natl Acad Sci USA* 105(36):16538-13543, 2008.

(Continued)

Primary Examiner — Bao Q Li
(74) Attorney, Agent, or Firm — Klarquist Sparkman, LLP

(57) ABSTRACT

Described herein is the generation of optimized H5N1 influenza HA polypeptides for eliciting a broadly reactive immune response to H5N1 influenza virus isolates. The optimized HA polypeptides were developed through a series of HA protein alignments, and subsequent generation of consensus sequences, based on human and avian H5N1 isolates. Provided herein are optimized H5N1 HA polypeptides, and compositions, fusion proteins and VLPs comprising the HA polypeptides. Further provided are codon-optimized nucleic acid sequences encoding the HA polypeptides. Methods of eliciting an immune response against influenza virus in a subject are also provided by the present disclosure.

14 Claims, 17 Drawing Sheets

Specification includes a Sequence Listing.

(56) References Cited

OTHER PUBLICATIONS

Ekiert et al., "Antibody recognition of a highly conserved influenza virus epitope: implications for universal prevention and therapy," *Science* 324(5924):246-251, 2009.
Fenimore et al., "Designing and Testing Broadly-Protective Filoviral Vaccines Optimized for Cytotoxic T-Lymphocyte Epitope Coverage," *PLoS One* 7(10):e44769, 2012.
Giles and Ross "A Computationally Optimized Broadly Reactive Antigen (COBRA) Based H5N1 VLP Vaccine Elicits Broadly Reactive Antibodies in Mice and Ferrets," *Vaccine*, vol. 29:3043-3054, 2011.
Giles et al., "Antibody Breadth and Protective Efficacy are Increased by Vaccination with Computationally Optimized Hemagglutinin but not with Polyvalent Hemagglutinin-Based H5N1 Virus-Like Particle Vaccines," *Clin. Vaccine Immunol.*, vol. 19:128-139, 2012.
Giles et al., "A Computationally Optimized Hemagglutinin Virus-Like Particle Elicits Broadly Reactive Antibodies that Protect Nonhuman Primates from H5N1 Infection," *J Infect Dis* 205(10):1562-1570, 2012.
Giles and Ross, "Computationally Optimized Antigens to Overcome Influenza Viral Diversity," *Expert Review of Vaccines*, vol. 11:267-269, 2012.
GenBank Accession No. ABA55715, Oct. 8, 2005.
GenBank Accession No. ABC66569, Mar. 29, 2006.
GenBank Accession No. ABD60856.1, Mar. 2, 2006.
GenBank Accession No. ABF47748, Jun. 16, 2006.
GenBank Accession No. ABO44123, Mar. 22, 2007.
GenBank Accession No. ABQ44416, May 16, 2007.
GenBank Accession No. ABU99095, May 1, 2008.
GenBank Accession No. ABW21677, Mar. 12, 2010.
GenBank Accession No. ACA48077, Mar. 18, 2008.
GenBank Accession No. EU195416, Mar. 12, 2010.
Guan et al., "H5N1 Influenza: A Protean Pandemic Threat", *Proc Natl Acad Sci USA*, vol. 101:8156-8161, 2004.
Jiang et al., "Enhanced Protective Efficacy of H5 Subtype Avian Influenza DNA Vaccine with Codon Optimized HA Gene in a pCAGGS Plasmid Vector," *Antiviral Res.*, vol. 75:234-241, 2007.
Laddy et al., "Immunogenicity of novel consensus-based DNA vaccines against avian influenza," *Vaccine* 25:2984-2989, 2007.
Office Action and Search Report in corresponding Chinese Application No. 201380009263.2, dated Jan. 20, 2016 (11 pages).
Parida et al., "Computational Analysis of Proteome of H5N1 Avian Influenza Virus to Define T Cell Epitopes with Vaccine Potential," *Vaccine*, vol. 25:7530-7539, 2007.
Prabakaran et al., "Neutralizing Epitopes of Influenza Virus Hemagglutinin: Target for the Development of a Universal Vaccine against H5N1 Lineages," *J Virol* 84(22):11822-11830, 2010.
Pushko et al., "Recombinant H1N1 Virus-Like Particle Vaccine Elicits Protective Immunity in Ferrets Against the 2009 Pandemic H1N1 Influenza Virus," *Vaccine*, vol. 28:4771-4776, 2010.
Somvanshi et al., "Prediction of Epitopes in Hemagglutinin and Neuraminidase Proteins of Influenza A Virus H5N1 Strain: A Clue for Diagnostic and Vaccine Development," *OMICS* vol. 12:61-69, 2008.
Tang et al., "Hemagglutinin Displayed Baculovirus Protects Against Highly Pathogenic Influenza," *Vaccine*, vol. 28:6821-6831, 2010.
Tang et al., "Characterization of Duck H5N1 Influenza Viruses with Differing Pathogenicity in Mallard (*Anas platyrhynchos*) Ducks," *Avian Pathol.*, vol. 38:457-467, 2009.
Tao et al., "Virus-Like Particle Vaccine Comprised of the HA, NA, and M1 Proteins of an Avian Isolated H5N1 Influenza Virus Induces Protective Immunity Against Homologous and Heterologous Strains in Mice," *Viral Immunol.*, vol. 22:273-281, 2009.
UniProt Accession No. A4U6Y5, May 15, 2007.
Wang et al., "Hemagglutinin (HA) Proteins from H1 and H3 Serotypes of Influenza A Viruses Require Different Antigen Designs for the Induction of Optimal Protective Antibody Responses as Studied by Codon-Optimized HA DNA Vaccines," *J. Virol.*, vol. 80:11628-11637, 2006.
Wang et al., "Identification of the Progenitors of Indonesian and Vietnamese Avian Influenza A (H5N1) Viruses from Southern China," *J Virol* 82(7):3405-3414, 2008.
Weaver et al., "Protection against Divergent Influenza H1N1 Virus by a Centralized Influenza Hemagglutinin," *PLoS One* 6(3):e18314, Mar. 28, 2011.

* cited by examiner

FIG. 1

All H5 COBRA Generation

| 1st Layer | | 2nd Layer | 3rd Layer |
|---|---|---|---|
| Clade | Total | | |
| 0 | 123 | → | Clade 0 Consensus |
| 1 | 533 | → | Clade 1 Consensus |
| 2.1.1 | 37 | ↘ | |
| 2.1.2 | 42 | → Clade 2.1 Consensus ↘ | |
| 2.1.3 | 165 | ↗ | |
| 2.2 | 635 | → Clade 2.2 Consensus → | |
| 2.3.1 | 17 | ↘ | Clade 2 Consensus |
| 2.3.2 | 73 | → Clade 2.3 Consensus ↗ | |
| 2.3.3 | 6 | ↗ | |
| 2.3.4 | 193 | ↗ | |
| 2.4 | 27 | → Clade 2.4 Consensus | |
| 2.5 | 18 | → Clade 2.5 Consensus | |
| 3 | 8 | → | Clade 3 Consensus |
| 4 | 14 | → | Clade 4 Consensus |
| 5 | 28 | → | Clade 5 Consensus |
| 6 | 9 | → | Clade 6 Consensus |
| 7 | 16 | → | Clade 7 Consensus |
| 8 | 9 | → | Clade 8 Consensus |
| 9 | 35 | → | Clade 9 Consensus |

All H5 COBRA (1989)

FIG. 3

1A HAI
HAI Titers to H5N1

Legend:
- ☐ Human COBRA-2
- ■ Human-Avian COBRA-2
- ▨ All H5 COBRA
- ▦ Whooper Swan VLP Y-axis: Log 2 HAI Titer X-axis (Viral Strain):
- Clade 1 (VN/1203/04)
- Clade 2.1.3 (IN/05/05)
- Clade 2.2 (WS/244/05)
- Clade 2.2 (TK/TK/05)
- Clade 2.2.1 (Eg/321/07)
- Clade 2.3.4 (EG/3300/08)
- Clade 2.3.4 (AN/1/05)
- Clade 2.3.4 (JWE/1031/06)
- Clade 7 (CK/VN/08)

FIG. 4

COBRA Study 1A Indonesia Challenge

FIG. 5

COBRA Study 1A Vietnam Challenge

Vietnam Clade 1 Challenge 5000pfu

- Human COBRA-2 VLP
- Human-Avian COBRA-2
- All H5 COBRA VLP
- Whooper Swan VLP
- Naive

FIG. 6

COBRA Study 1A Indonesia Viral Titers
Day 3

FIG. 7

COBRA Study 1A Vietnam Viral Titers
Day 3

FIG. 8

COBRA Study 2A Vietnam Challenge

2A Vietnam Clade 1 Challenge 5000pfu

- Human COBRA-2
- Human-Avian COBRA-2
- All H5 COBRA
- Whooper Swan VLP
- Naive

% Original Weight vs Days Post Infection

FIG. 9

COBRA Study 2A Vietnam Viral Titers
Day 2 and 3

COBRA Study 4A Percent Survival

FIG. 13

COBRA Study 5A Viral Titers Day 2

FIG. 14

COBRA Study 5A Viral Titers Day 3

FIG. 15

COBRA Study 9A Whooper Swan Challenge

FIG. 16

COBRA Study 9A Viral Titers Day 2

FIG. 17

COBRA Study 9A Viral Titers Day 3

SEQUENCE LISTING

```
<160> NUMBER OF SEQ ID NOS: 4

<210> SEQ ID NO 1
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
            100                 105                 110
```

```
Asp Tyr Glu Glu Leu Lys His Leu Leu Ser Arg Ile Asn His Phe Glu
            115                 120                 125
Lys Ile Gln Ile Ile Pro Lys Ser Ser Trp Ser Asn His Glu Ala Ser
        130                 135                 140
Ser Gly Val Ser Ser Ala Cys Pro Tyr Gln Gly Lys Ser Ser Phe Phe
145                 150                 155                 160
Arg Asn Val Val Trp Leu Ile Lys Lys Asn Ser Ala Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Lys Leu Tyr Gln
        195                 200                 205
Asn Pro Thr Thr Tyr Ile Ser Val Gly Thr Ser Thr Leu Asn Gln Arg
210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Lys Ser Glu Leu Glu Tyr Gly
        275                 280                 285
Asn Cys Asn Thr Lys Cys Gln Thr Pro Met Gly Ala Ile Asn Ser Ser
        290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
        370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
        450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
Arg Leu Lys Arg Glu Glu Ile Ser Gly Val Lys Leu Glu Ser Ile Gly
        515                 520                 525
```

Thr Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile
                565

<210> SEQ ID NO 2
<211> LENGTH: 1736
<212> TYPE: DNA
<213> ORGANISM: Artificial Sequence
<220> FEATURE:
<223> OTHER INFORMATION: Synthetic polynucleotide

<400> SEQUENCE: 2

| | | | | | |
|---|---|---|---|---|---|
| atggaaaaga | tcgtgctgct | gctggccatc | gtgtccctgg | tgaagagcga | ccagatttgc | 60 |
| attggctacc | acgccaacaa | tagcacagag | caggtggaca | ccatcatgga | aaaaacgtg | 120 |
| accgtgaccc | acgcccagga | catcctggag | aaaacccaca | cggcaagct | gtgtgacctg | 180 |
| gacggcgtga | agcccctgat | cctgagagac | tgctccgtgg | ccggctggct | gctgggcaac | 240 |
| cccatgtgtg | acgagttcat | caacgtgccc | gagtggagct | acatcgtgga | aaggccagc | 300 |
| cccgccaacg | acctgtgcta | ccccggcgac | ttcaacgact | acgaggagct | gaagcacctg | 360 |
| ctgtcccgga | tcaaccactt | cgagaagatc | cagatcatcc | ccaagagcag | ctggagcaac | 420 |
| cacgaggcca | gcagcggcgt | gtccagcgcc | tgccctacc | agggcaagag | cagcttcttc | 480 |
| cggaacgtgg | tctggctgat | caagaagaac | tctgcctatc | ccaccatcaa | gcggagctac | 540 |
| aacaacacca | ccaggagga | tctgctggtc | ctgtggggca | tccaccaccc | caacgacgcc | 600 |
| gccgagcaga | ccaagctgta | ccagaacccc | accacctaca | tcagcgtggg | caccagcacc | 660 |
| ctgaaccagc | ggctggtgcc | caagatcgcc | accggtcca | agtgaacgg | ccagagcggc | 720 |
| cggatggaat | tcttctggac | catcctgaag | cccaacgatg | ccatcaactt | cgagagcaac | 780 |
| ggcaacttca | tcgcccccga | gtacgcctac | aagatcgtga | agaagggcga | cagcgccatc | 840 |
| atgaagagcg | agctggaata | cggcaactgc | aacaccaagt | gccagacccc | catgggcgcc | 900 |
| atcaacagca | gcatgccctt | ccacaacatc | cacccctga | ccatcggcga | gtgccccaag | 960 |
| tacgtgaaga | gcaacaggct | ggtgctggcc | accggcctgc | ggaacagccc | ccagcgggag | 1020 |
| cggcggagga | agaagcgggg | cctgttcggc | gccatcgccg | gcttcatcga | gggcggctgg | 1080 |
| cagggcatgg | tggacgggtg | gtacggctac | caccacagca | atgagcaggg | cagcggctac | 1140 |
| gccgccgaca | agagagcac | ccagaaggcc | atcgacggcg | tcaccaacaa | ggtgaacagc | 1200 |
| atcatcgaca | agatgaacac | ccagttcgag | gccgtgggcc | gggagttcaa | caacctggaa | 1260 |
| cggcggatcg | agaacctgaa | caagaaaatg | gaagatggct | tcctggacgt | gtggaccta c | 1320 |
| aacgccgaac | tcctggtgct | gatggaaaac | gagcggaccc | tggacttcca | cgacagcaac | 1380 |
| gtgaagaacc | tgtacgacaa | agtgcggctg | cagctgcggg | acaacgccaa | agagctgggc | 1440 |
| aacggctgct | tcgagttcta | ccacaagtgc | gacaacgagt | gcatggaaag | cgtgcggaac | 1500 |
| ggcacctacg | actaccccca | gtacagcgag | gaagcccggc | tgaagcggga | ggaaatcagc | 1560 |
| ggcgtgaaac | tggaaagcat | cggcacctac | cagatcctga | gcatctacag | caccgtggcc | 1620 |
| agcagcctcg | ctctgccat | tatggtggcc | ggcctgagcc | tgtggatgtg | cagcaacggc | 1680 |
| agcctgcagt | gccggatcgg | atccagatct | gctagcgtcg | actctagatt | aattaa | 1736 |

<210> SEQ ID NO 3
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 3

```
Met Glu Lys Ile Val Leu Leu Ala Ile Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365
```

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
530                 535                 540

Ala Ile Met Val Ala Gly Leu Ser Leu Trp Met Cys Ser Asn Gly Ser
545                 550                 555                 560

Leu Gln Cys Arg Ile Cys Ile
            565

<210> SEQ ID NO 4
<211> LENGTH: 1739
<212> TYPE: DNA
<213> ORGANISM: Artificial Sequence
<220> FEATURE:
<223> OTHER INFORMATION: Syntheric polynucleotide

<400> SEQUENCE: 4

```
atggagaaga tcgtgctgct gctggccatc gtgtccctgg tgaagagcga ccagatttgc      60
atcggctacc acgccaacaa tagcaccgag caagtggaca ccatcatgga gaaaaacgtg     120
accgtgaccc acgctcagga catcctcgaa aaacccaca  acggcaagct gtgcgatctg     180
gacggcgtga agcccctgat cctgagagac tgcagcgtgg ccggctggct gctgggcaat     240
cccatgtgcg acgagttcat caacgtgccc gagtggagct acatcgtgga aggccaaac     300
cccgccaacg acctgtgcta ccccggcaac ttcaacgact acgaggagct gaagcacctg     360
ctgagccgga tcaaccactt cgagaagatc cagatcatcc caagagcag ctggagcgac      420
catgaggcaa gcagcggcgt gtccagcgcc tgccccctacc agggcaagtc cagcttcttc     480
cgcaacgttg tgtggctgat caagaagaac agcgcctacc caccatcaa gcggagctac      540
aacaacacca accaggagga cctgctggtc ctgtggggca tccaccaccc caacgacgcc     600
gccgagcaga cccggctgta ccagaacccc accacctaca tctctgtggg caccagcacc     660
ctgaaccagc ggctggtgcc caagatcgcc acccggagca aggtgaacgg ccagagcggc     720
cggatggagt tcttctggac catcctgaag cccaacgatg ccatcaactt cgagagcaac     780
ggcaacttca tcgcccccga gtacgcctac aagatcgtga agaagggcga cagcgccatc     840
atgaagtccg agctggagta cggcaactgt aacaccaagt gccagacccc catgggcgcc     900
```

-continued

```
atcaacagca gcatgccctt ccacaacatc cacccctga ccatcggcga gtgccccaag      960
tacgtgaaga gcaacaggct ggtgctggcc accggcctga gaaacagccc ccagagagag    1020
cggagaagaa agagaggcct gttcggcgcc attgccggct tcatcgaggg cggctggcag    1080
ggcatggtgg acgggtggta cggctaccac cactccaacg agcagggcag cggctacgcc    1140
gccgacaaag agagcaccca gaaagctatc gacggcgtga ccaacaaagt gaacagcatc    1200
atcgacaaga tgaataccca gttcgaggcc gtgggcagag agttcaacaa cctggaaaga    1260
agaatcgaga acctgaacaa gaaaatggaa gatggctttc tggatgtgtg gacctacaac    1320
gccgagctgc tggtgctgat ggaaaacgag cggaccctgg acttccacga cagcaacgtg    1380
aagaatctgt acgacaaagt gcggctgcag ctgagagaca cgccaaaga gctgggcaac     1440 ggctgcttcg agttctacca caagtgcgac aatgagtgca tggaaagcgt gcggaacggc    1500
acctacgact accccagta cagcgaggaa gcccggctga agagagaaga gatttccggc     1560
gtgaagctgg aaagcatcgg cacctaccag atcctgagca tctacagcac cgtggccagc    1620
agcctggccc tggccatcat ggtggccggc ctgagcctgt ggatgtgcag caacggcagc    1680
ctgcagtgcc ggatctgcat cggatccaga tctgctagcg tcgactctag attaattaa    1739
```

COMPUTATIONALLY OPTIMIZED BROADLY REACTIVE ANTIGENS FOR HUMAN AND AVIAN H5N1 INFLUENZA

CROSS REFERENCE TO RELATED APPLICATIONS

This is a divisional of U.S. application Ser. No. 14/377,633, filed Aug. 8, 2014, issued as U.S. Pat. No. 9,566,327 on Aug. 8, 2014, which is the U.S. National Stage of International Application No. PCT/US2013/025284, filed Feb. 8, 2013, published in English under PCT Article 21(2), which claims the benefit of U.S. Provisional Application No. 61/597,998, filed Feb. 13, 2012. The above-referenced applications are herein incorporated by reference in their entirety.

FIELD

This disclosure concerns optimized influenza hemagglutinin proteins that elicit broadly reactive immune responses to human and avian H5N1 influenza viruses, and their use as vaccines.

BACKGROUND

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2). The HA, NA, M1, and M2 are membrane associated, whereas NP, PB1, PB2, PA, and NS2 are nucleocapsid associated proteins. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Each year, seasonal influenza causes over 300,000 hospitalizations and 36,000 deaths in the U.S. alone (Simonsen et al., *Lancet Infect Dis* 7:658-66, 2007). The emergence of the novel H1N1 influenza virus in 2009 demonstrated how quickly a new influenza pandemic can sweep across the world.

There are currently two influenza vaccine approaches licensed in the United States—the inactivated, split vaccine and the live-attenuated virus vaccine. The inactivated vaccines can efficiently induce humoral immune responses but generally only poor cellular immune responses. Live virus vaccines cannot be administered to immunocompromised or pregnant patients due to their increased risk of infection. Thus, a need exists for a broadly protective influenza virus vaccine.

SUMMARY

Disclosed herein is the generation of computationally-optimized H5N1 HA polypeptides for eliciting a broadly reactive immune response to H5N1 influenza virus. The optimized HA polypeptides were developed through a series of HA protein alignments, and subsequent generation of consensus sequences based on 1,989 human and avian H5N1 influenza isolates.

Provided herein are recombinant influenza HA polypeptides having an optimized amino acid sequence for eliciting a broadly reactive immune response against H5N1 influenza. In some embodiments, the HA polypeptide comprises an amino acid sequence at least 99.8% identical to SEQ ID NO: 1 or at least 99.6% identical to SEQ ID NO: 3. In some embodiments, the amino acid sequence of the polypeptide comprises no more than two, or no more than one substitution relative to SEQ ID NO: 1 or SEQ ID NO: 3. In some embodiments, the influenza HA polypeptide lacks the N-terminal methionine residue.

Isolated nucleic acid molecules and vectors encoding the recombinant HA polypeptides are also provided by the present disclosure. In some embodiments, the nucleic acid molecules and vectors encoding the recombinant HA polypeptides comprise the nucleotide sequence of SEQ ID NO: 2 or SEQ ID NO: 4. Further provided are isolated cells comprising such vectors.

Also provided are influenza virus-like particles (VLPs) and fusion proteins comprising the optimized HA polypeptides disclosed herein.

Further provided are compositions that include the optimized influenza HA polypeptides, fusion proteins or VLPs disclosed herein in a pharmaceutically acceptable carrier. Methods of eliciting an immune response against influenza virus in a subject by administering the disclosed compositions, fusion proteins or VLPs are also provided by the present disclosure.

Also provided are methods of immunizing a subject against influenza virus by administering to the subject a composition comprising a VLP that contains an optimized HA polypeptide.

The foregoing and other objects, features, and advantages of the invention will become more apparent from the following detailed description, which proceeds with reference to the accompanying figures.

BRIEF DESCRIPTION OF THE DRAWINGS

FIG. 1 is a schematic summarizing the process for generating a COBRA HA sequence using 1989 human and avian H5N1 influenza virus isolates, referred to herein as "All H5 COBRA" HA.

FIG. 3 is a graph showing HAI titers against clade 1, clade 2 and clade 7 challenge strains following vaccination with VLPs containing the All H5 COBRA HA sequence (SEQ ID NO: 1), VLPs containing the Human-Avian COBRA-2 HA sequence (SEQ ID NO: 3), VLPs containing a human clade 2 influenza virus COBRA HA sequence (Human COBRA-2), or VLPs containing Whooper Swan (A/Whooper Swan/Mongolia/244/2005) influenza virus HA. Vaccinations (3 μg) were performed at 0 and 3 weeks with adjuvant (Imject™).

FIG. 4 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs and subsequently challenged with Indonesia clade 2.1 virus (A/Indonesia/5/2005). Vaccinations (3 μg)

Figure 2:
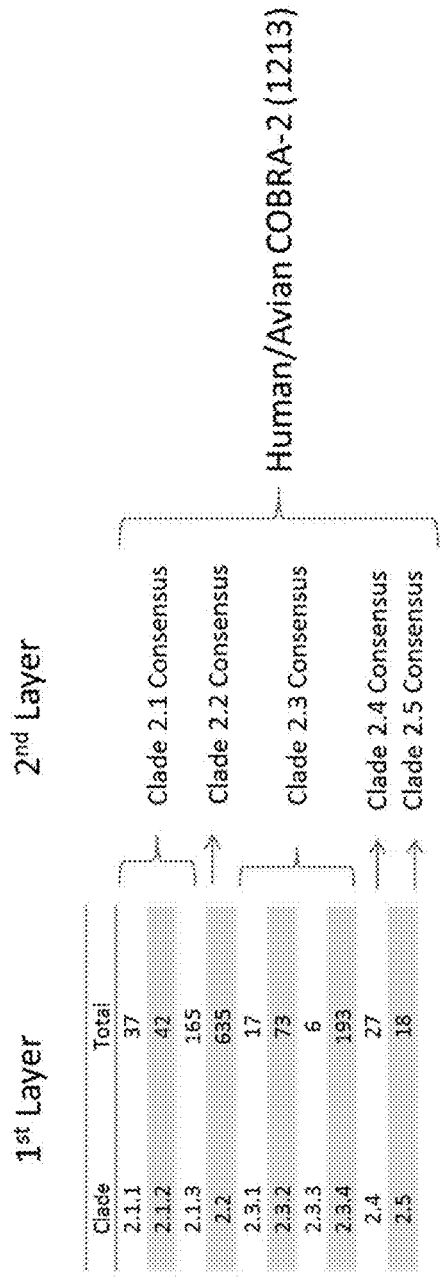
FIG. 2 is a schematic summarizing the process for generating a COBRA HA sequence using 1213 human and avian H5N1 clade 2 isolates, referred to herein as "Human-Avian COBRA-2" HA.

were performed at 0 and 3 weeks with adjuvant (Imject™); virus challenge occurred during week 5.

FIG. 5 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus (A/Vietnam/1203/2004). Vaccinations (3 µg) were performed at 0 and 3 weeks with adjuvant (Imject™); virus challenge occurred during week 5.

Figure 6:
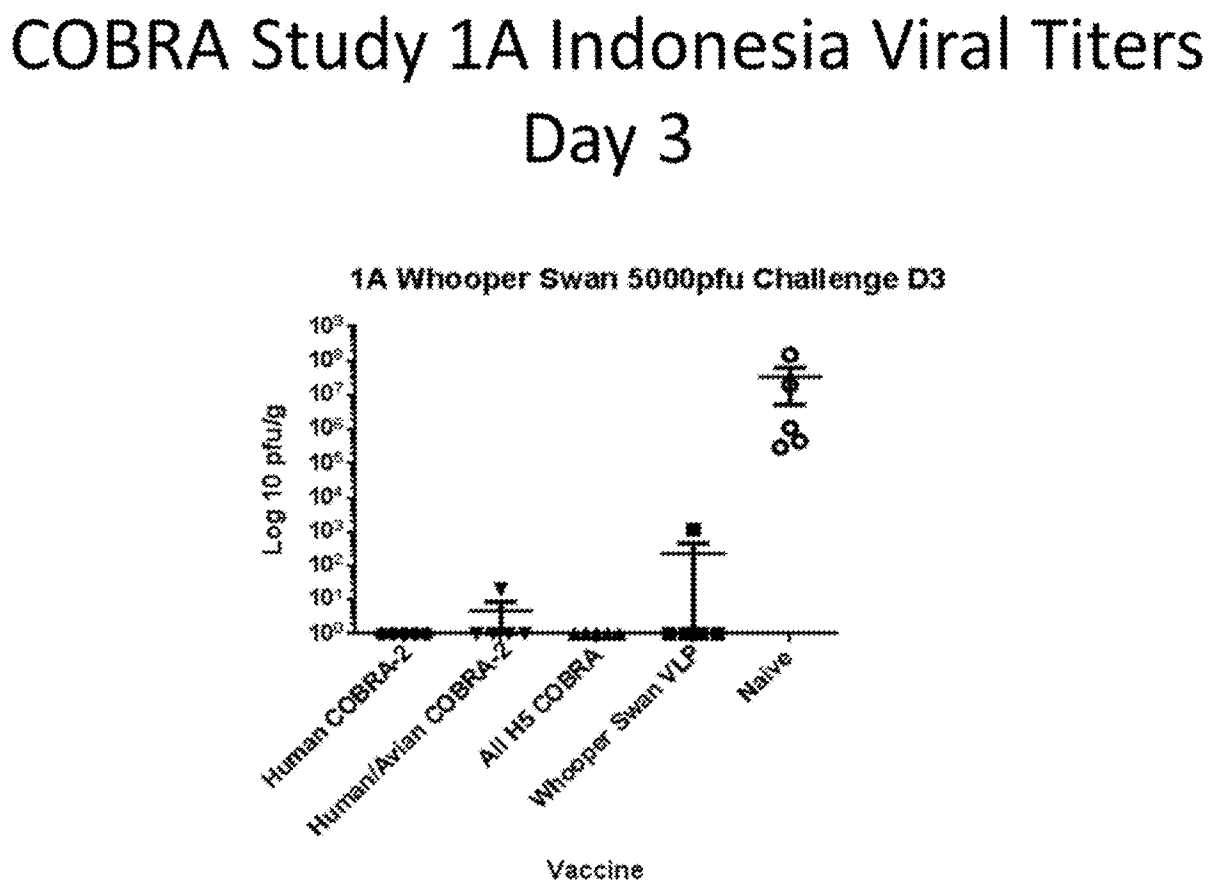

FIG. 6 is a graph showing viral titers (Day 3) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Whooper Swan clade 2.2 virus. Vaccinations (3 µg) were performed at 0 and 3 weeks with adjuvant (Imject™); virus challenge occurred during week 5.

Figure 7:
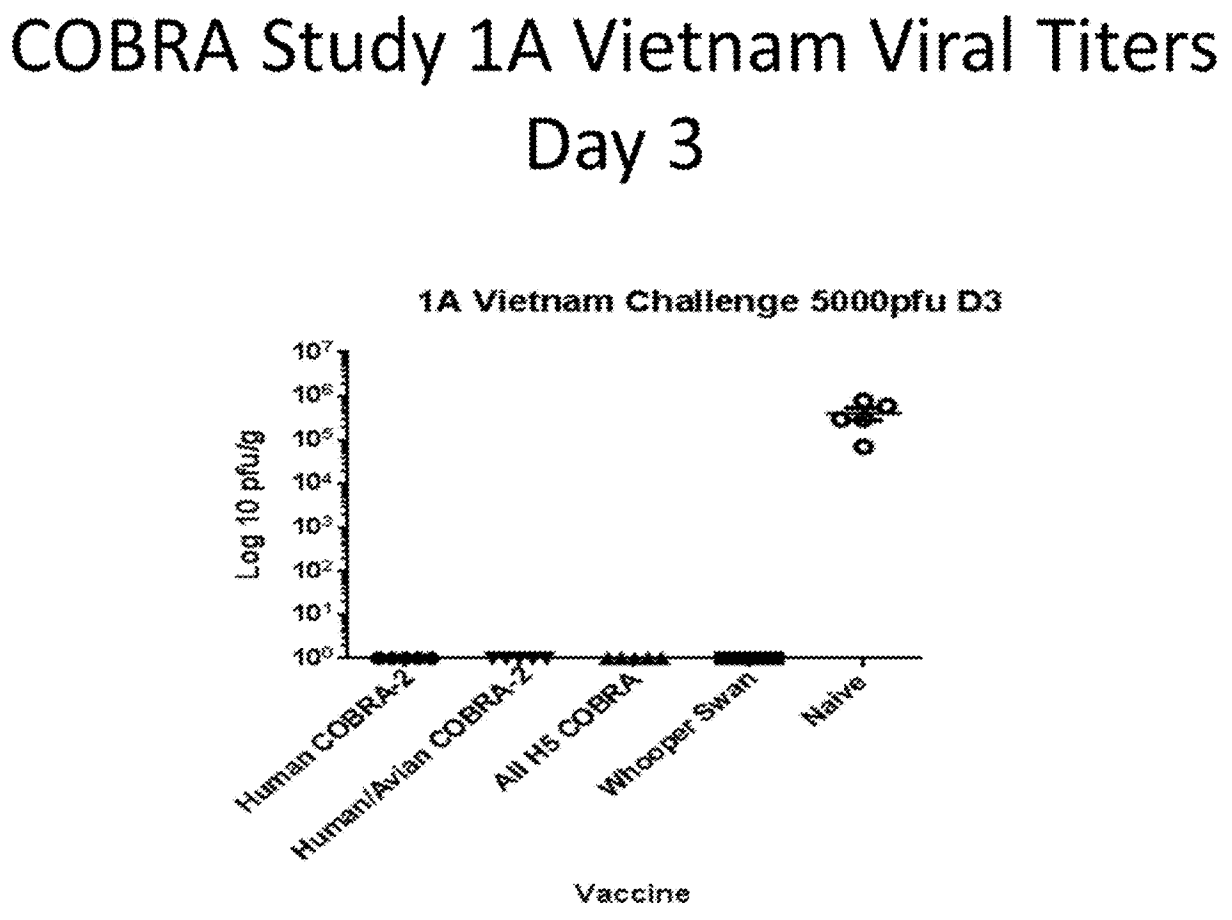

FIG. 7 is a graph showing viral titers (Day 3) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. Vaccinations (3 µg) were performed at 0 and 3 weeks with adjuvant (Imject™); virus challenge occurred during week 5.

FIG. 8 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination (3 µg) was performed at week 0 with adjuvant (Imject™), followed by virus challenge during week 4.

Figure 9:
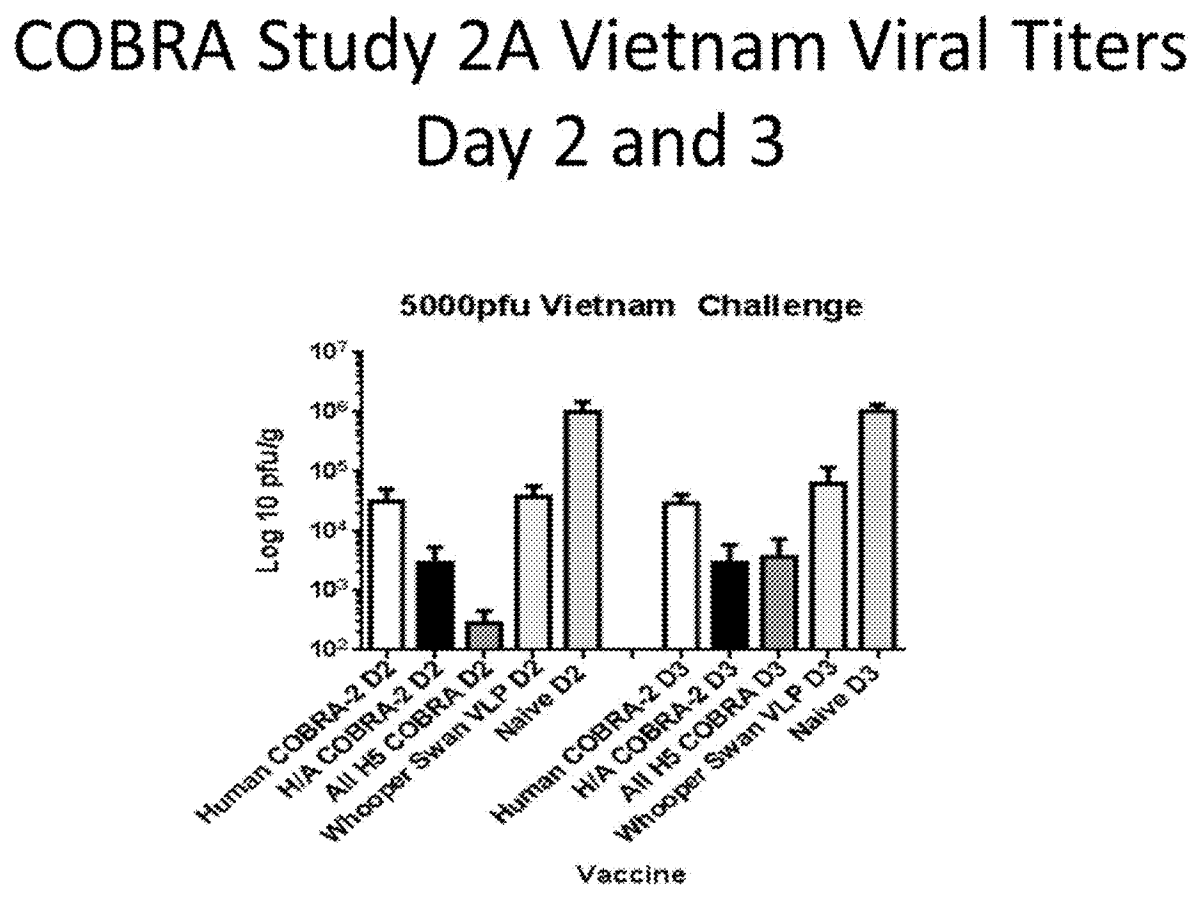

FIG. 9 is a graph showing viral titers in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination (3 µg) was performed at week 0 with adjuvant (Imject™), followed by virus challenge during week 4. D2=day 2; D3=day 3.

Figure 10:
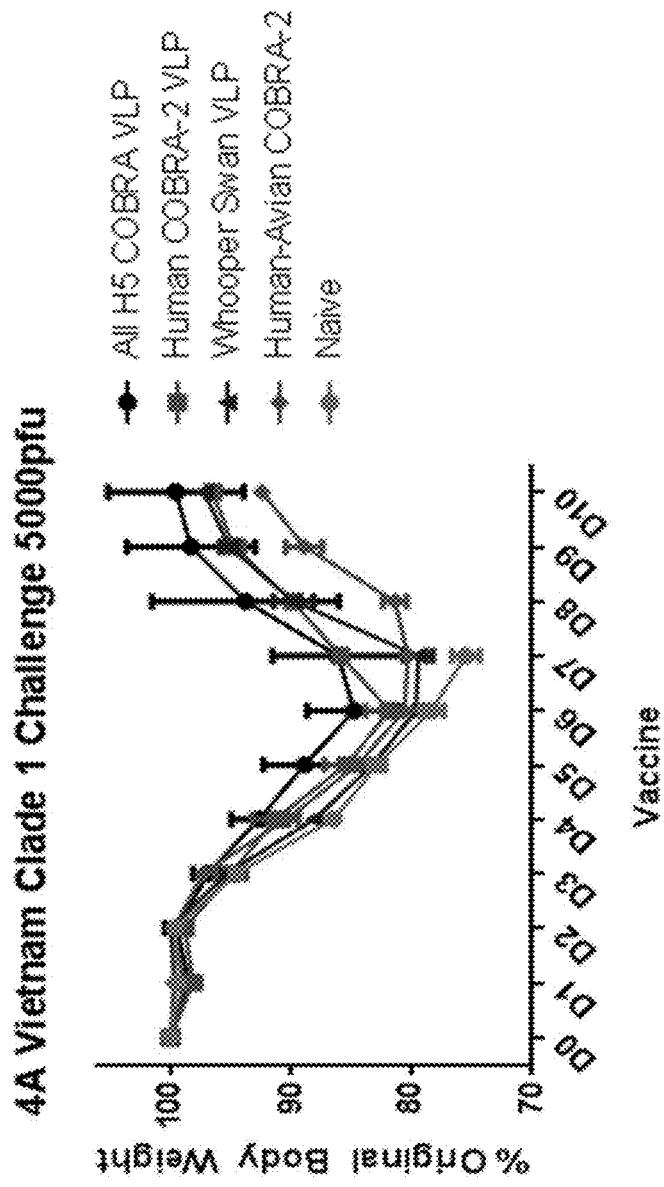

FIG. 10 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination (3 µg) was performed at week 0 without adjuvant, followed by virus challenge during week 4.

Figure 11:
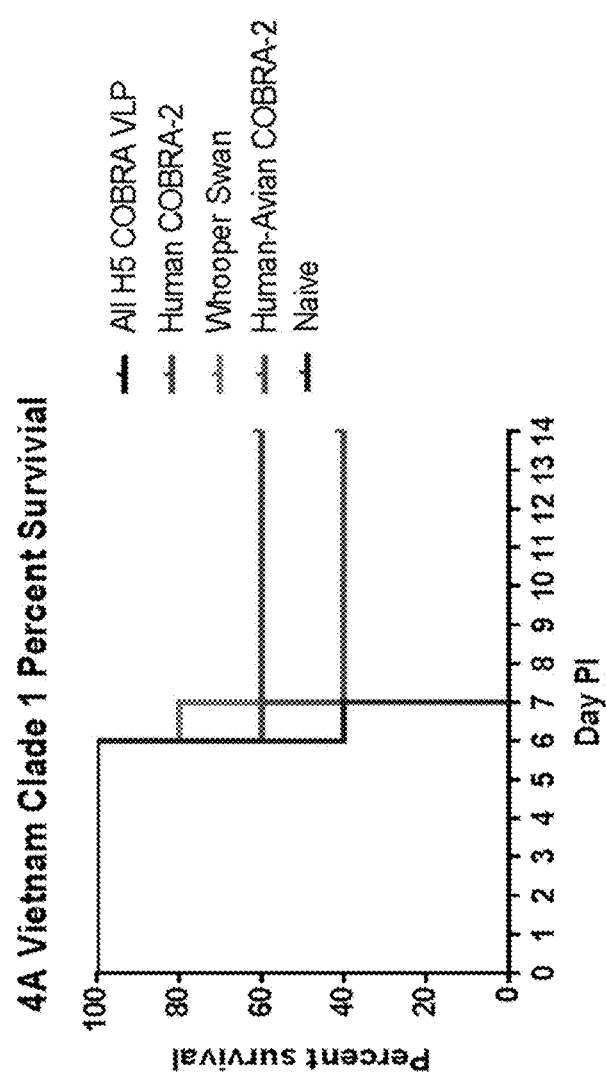

FIG. 11 is a graph showing percent survival of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination (3 µg) was performed at week 0 without adjuvant, followed by virus challenge during week 4.

Figure 12:
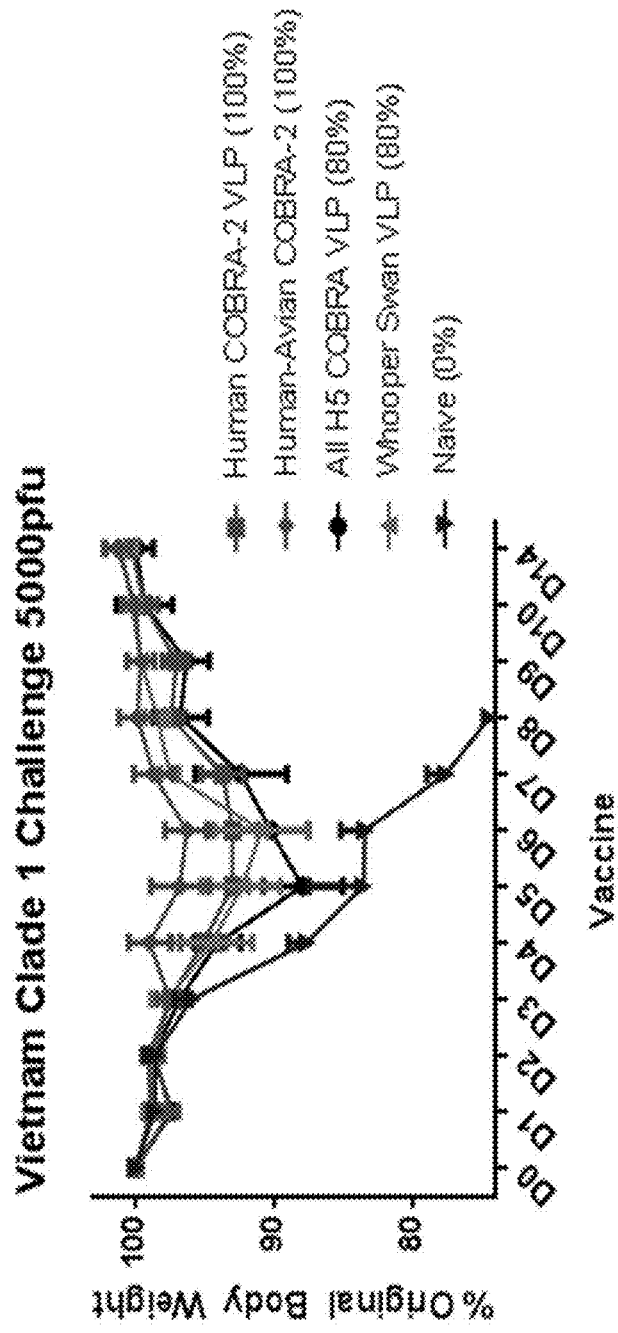

FIG. 12 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination at a dose of 0.6 µg was performed at week 0 with adjuvant (Imject™), followed by virus challenge during week 4.

Figure 13:
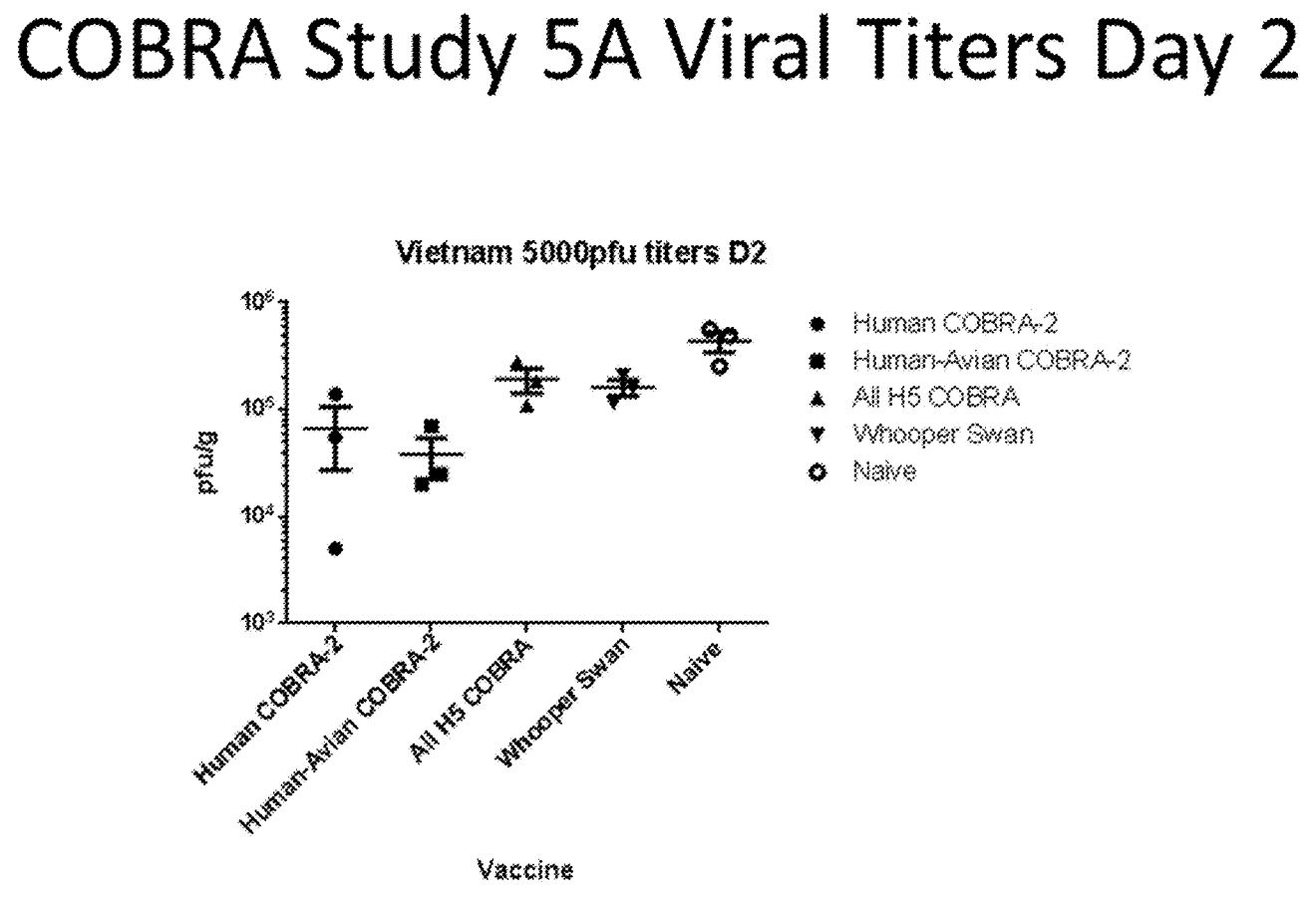

FIG. 13 is a graph showing viral titers (Day 2) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination at a dose of 0.6 µg was performed at week 0 with adjuvant (Imject™), followed by virus challenge during week 4.

Figure 14:
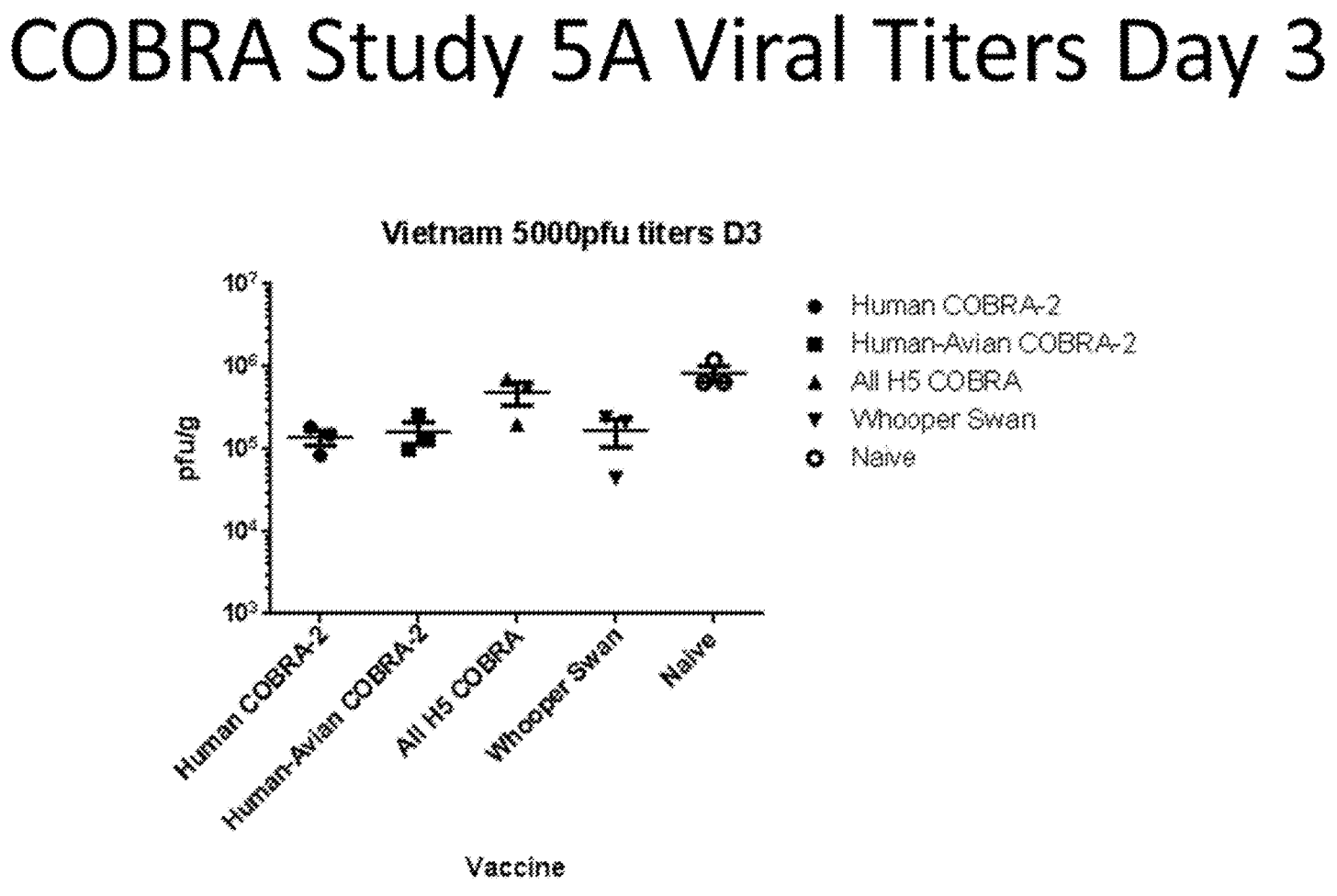

FIG. 14 is a graph showing viral titers (Day 3) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Vietnam clade 1 virus. A single vaccination at a dose of 0.6 µg was performed at week 0 with adjuvant (Imject™), followed by virus challenge during week 4.

Figure 15:
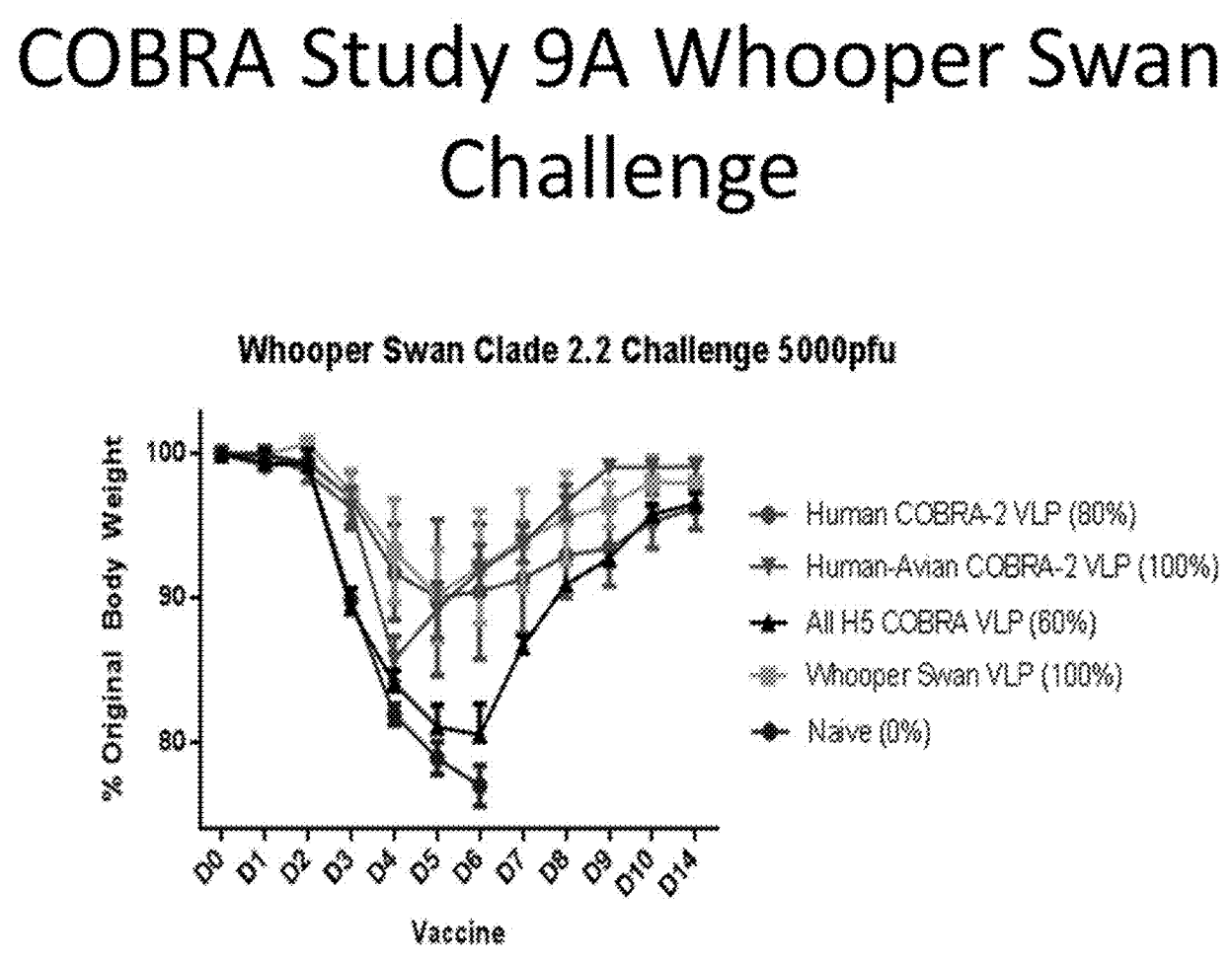

FIG. 15 is a graph showing body weight of animals vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Whooper Swan clade 2.2 virus. A single vaccination at a dose of 0.6 µg was performed at week 0 with adjuvant (Imject™), followed by virus challenge during week 4.

Figure 16:
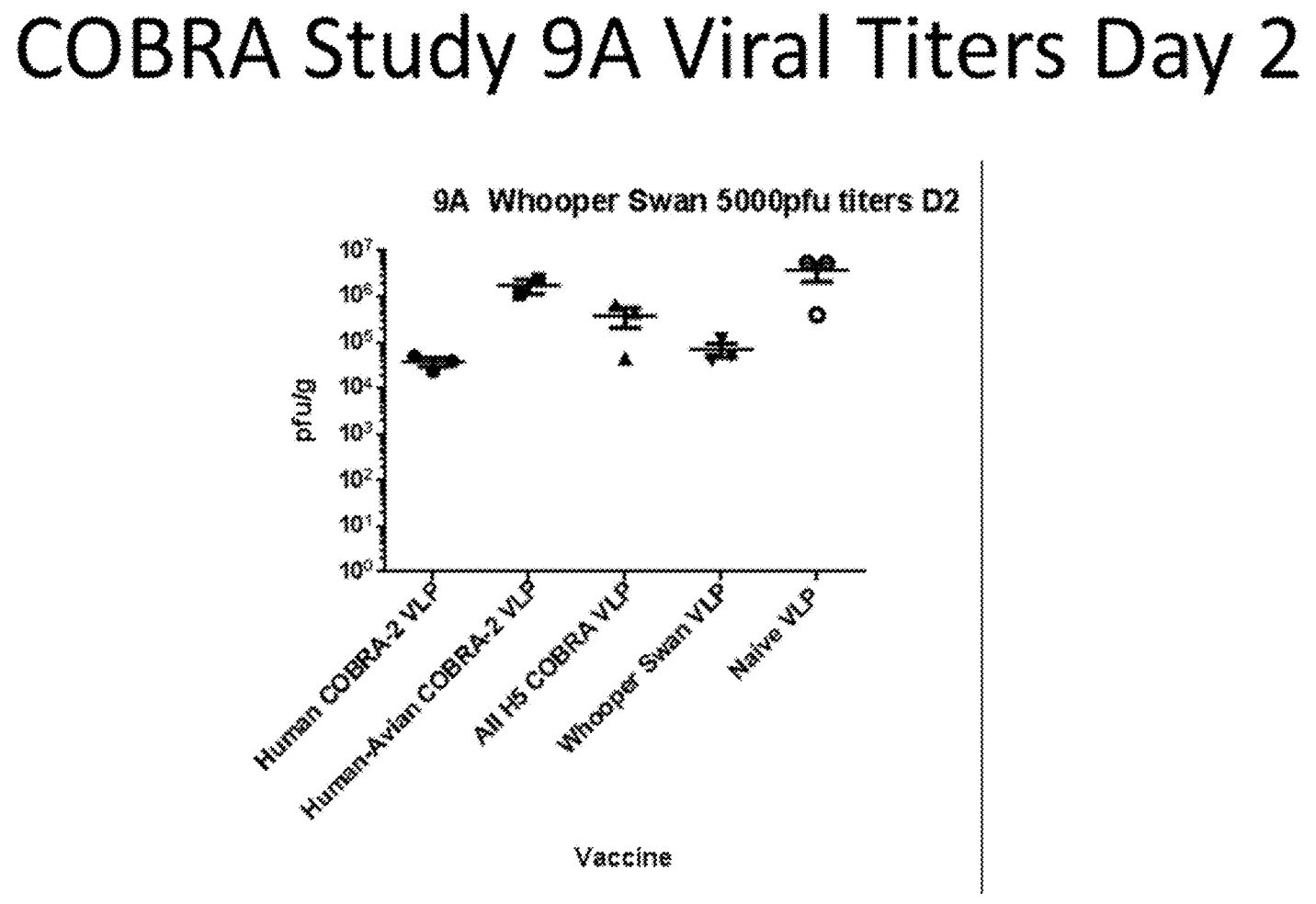

FIG. 16 is a graph showing viral titers (Day 2) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Whooper Swan clade 2.2 virus. A single vaccination at a dose of 0.6 µg was performed at week 0 with adjuvant (Imject™), followed by virus challenge during week 4.

Figure 17:
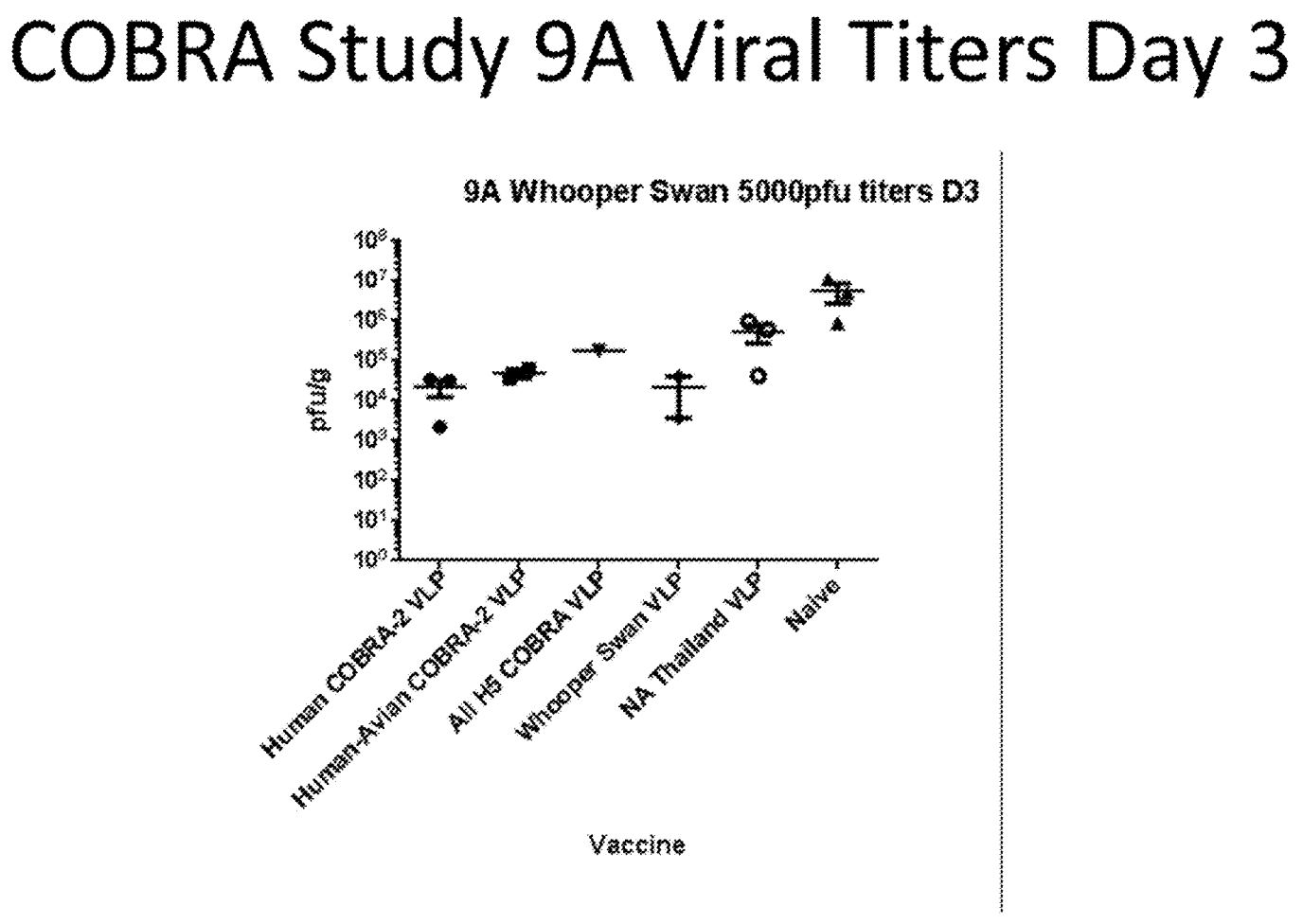

FIG. 17 is a graph showing viral titers (Day 3) in lungs of mice vaccinated with VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or Whooper Swan VLPs, and subsequently challenged with Whooper Swan clade 2.2 virus. A single vaccination at a dose of 0.6 µg was performed at week 0 with adjuvant (Imject™), followed by virus challenge during week 4.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 20, 2016, 14.7 KB, which is incorporated by reference herein. In the accompanying sequence listing:

SEQ ID NO: 1 is a COBRA amino acid sequence for human and avian H5N1 influenza isolates, referred to herein as "All H5 COBRA" HA.

SEQ ID NO: 2 is a codon-optimized nucleic acid sequence encoding the H5N1 influenza COBRA HA of SEQ ID NO: 1.

SEQ ID NO: 3 is a COBRA amino acid sequence for human and avian H5N1 clade 2 influenza isolates, referred to herein as "Human-Avian COBRA-2" HA.

SEQ ID NO: 4 is a codon-optimized nucleic acid sequence encoding the H5N1 influenza COBRA HA of SEQ ID NO: 2.

DETAILED DESCRIPTION

I. Abbreviations

COBRA: computationally optimized broadly reactive antigen
HA: hemagglutinin
HAI: hemagglutination inhibition
HRP: horseradish peroxidase
M1: matrix protein 1
NA: neuraminidase
PFU: plaque form unit
VLP: virus-like particle II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza HA protein.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells. Codon optimization does not alter the amino acid sequence of the encoded protein.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons. For example, a fusion protein can include an influenza HA fused to a heterologous protein.

Hemagglutinin (HA): An influenza virus surface glycoprotein. HA mediates binding of the virus particle to a host cells and subsequent entry of the virus into the host cell. The nucleotide and amino acid sequences of numerous influenza HA proteins are known in the art and are publically available, such as through the NCBI Influenza Virus Resource database (Bao et al., *J Virol* 82:596-601, 2008). HA (along with NA) is one of the two major influenza virus antigenic determinants.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen (such as an HA polypeptide).

Immunize: To render a subject protected from an infectious disease, such as by vaccination.

Influenza virus: A segmented negative-strand RNA virus that belongs to the Orthomyxoviridae family. There are three types of influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses (or VLPs), as well as chemically synthesized nucleic acids or peptides.

Linker: One or more amino acids that serve as a spacer between two polypeptides of a fusion protein.

Matrix (M1) protein: An influenza virus structural protein found within the viral envelope. M1 is thought to function in assembly and budding.

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Optimized influenza HA protein: As used herein, "optimized influenza HA protein" refers to an HA protein consensus sequence generated by sequence alignments of human and avian H5N1 influenza viruses isolates (as described in Examples 1 and 2 below). Nucleotide sequences encoding optimized HA proteins are further optimized for expression in mammalian cells via codon-optimization and RNA optimization (such as to increase RNA stability). Optimized influenza HA proteins disclosed herein (and set forth herein as SEQ ID NO: 1 and SEQ ID NO: 3) are also referred to as "COBRA" (computationally-optimized broadly reactive antigen) sequences. Optimized HA polypeptides are designed to elicit broadly reactive immune responses in a subject. In the context of the present disclosure, "broadly reactive" means the protein sequence elicits an immune response in a subject that is sufficient to inhibit, neutralize or prevent infection of a broad range of influenza viruses (such as most or all influenza viruses within a specific subtype). In some instances, the optimized influenza HA protein is capable of eliciting an immune response, such as a protective immune response, against most or all H5N1 influenza virus isolates.

Outbreak: As used herein, an influenza virus "outbreak" refers to a collection of virus isolates from within a single country in a given year.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a CMV promoter.

Purified: The term "purified" does not require absolute purity; rather, it is intended as a relative term. Thus, for example, a purified peptide, protein, virus, VLP or other active compound is one that is isolated in whole or in part from naturally associated proteins and other contaminants. In certain embodiments, the term "substantially purified" refers to a peptide, protein, virus, VLP or other active compound that has been isolated from a cell, cell culture medium, or other crude preparation and subjected to fractionation to remove various components of the initial preparation, such as proteins, cellular debris, and other components.

Recombinant: A recombinant nucleic acid, protein, virus or VLP is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates.

Therapeutically effective amount: A quantity of a specified agent sufficient to achieve a desired effect in a subject being treated with that agent. For example, this may be the amount of an influenza virus vaccine useful for eliciting an immune response in a subject and/or for preventing infection or disease caused by influenza virus. Ideally, in the context of the present disclosure, a therapeutically effective amount of an influenza vaccine is an amount sufficient to increase resistance to, prevent, ameliorate, and/or treat infection caused by influenza virus in a subject without causing a substantial cytotoxic effect in the subject. The effective amount of an influenza vaccine useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins (including VLPs), peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of an inserted gene or genes. In some embodiments of the present disclosure, the vector encodes an influenza HA, NA or M1 protein. In some embodiments, the vector is the pTR600 expression vector (U.S. Patent Application Publication No. 2002/0106798; Ross et al., *Nat Immunol.* 1(2):102-103, 2000; Green et al., *Vaccine* 20:242-248, 2001).

Virus-like particle (VLP): Virus particles made up of one of more viral structural proteins, but lacking the viral genome. Because VLPs lack a viral genome, they are non-infectious. In addition, VLPs can often be produced by heterologous expression and can be easily purified. Most VLPs comprise at least a viral core protein that drives budding and release of particles from a host cell. One example of such a core protein is influenza M1. In some embodiments herein, an influenza VLP comprises the HA, NA and/or M1 proteins. Influenza VLPs can be produced by transfection of host cells with plasmids encoding the HA and NA proteins, and optionally the M1 protein. After incubation of the transfected cells for an appropriate time to allow for protein expression (such as for approximately 72 hours), VLPs can be isolated from cell culture supernatants. Example 3 provides an exemplary protocol for purifying influenza VLPs from cell supernatants. In this example, VLPs are isolated by low speed centrifugation (to remove cell debris), vacuum filtration and ultracentrifugation through 20% glycerol. Other methods of producing influenza VLPs are known in the art (see, for example, U.S. Patent Application Publication Nos. 2006/0263804; 2008/0031895; 2010/0166769; and 2010/0239610).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the generation of computationally-optimized H5N1 HA polypeptides for eliciting a broadly reactive immune response to H5N1 influenza virus. The optimized HA polypeptides were developed through a series of HA protein alignments, and subsequent generation of consensus sequences based on 1,989 human and avian H5N1 influenza isolates. The methods used to generate the optimized HA consensus sequences are described in Examples 1 and 2, and shown in FIGS. 1 and 2. The amino acid sequences of two particular HA polypeptides are set forth herein as SEQ ID NO: 1 (All H5 COBRA) and SEQ ID NO: 3 (Human-Avian COBRA-2). Also disclosed herein are codon-optimized nucleic acid sequences encoding the optimized HA polypeptides. Two exemplary codon-optimized HA nucleic acid sequences are set forth herein as SEQ ID NO: 2 and SEQ ID NO: 4.

Provided herein are recombinant influenza HA polypeptides having an optimized amino acid sequence for eliciting a broadly reactive immune response against H5N1 influenza. In some embodiments, the HA polypeptide comprises an amino acid sequence at least 99.8% identical to residues 2-566 of SEQ ID NO: 1 or at least 99.6% identical to residues 2-567 of SEQ ID NO: 3. In particular examples, the amino acid sequence of the HA polypeptide comprises or consists of the amino acid sequence of residues 2-566 of SEQ ID NO: 1 or residues 2-567 of SEQ ID NO: 3.

In other embodiments, the recombinant HA polypeptide comprises an amino acid sequence at least 99.8% identical to SEQ ID NO: 1 or at least 99.6% identical to SEQ ID NO: 3. In some examples, the amino acid sequence of the HA polypeptide is more identical than the percentages identities described above. In other examples, the amino acid sequence comprises or consists of the amino acid sequence of SEQ ID NO: 1 or SEQ ID NO: 3. In particular examples, the HA polypeptide lacks the N-terminal methionine residue.

In some embodiments, the amino acid sequence of the HA polypeptide comprises no more than 1 amino acid substitution relative to SEQ ID NO: 1. In other embodiments, the amino acid sequence of the HA polypeptide comprises no more than 2, or no more than 1, amino acid substitutions relative to SEQ ID NO: 3. In some examples, the amino acid substitution is a conservative substitution. In other examples, the amino acid substitution is a non-conservative substitution. In other examples, the number of substitutions relative to the identified sequence is less than the number of substitutions identified above.

Further provided are isolated nucleic acid molecules encoding a recombinant influenza HA polypeptide disclosed herein. In some embodiments, the nucleic acid molecule is codon-optimized for expression in mammalian cells. The nucleic acid molecule is optionally further optimized for RNA stability.

In some embodiments, the sequence of the nucleic acid molecule encoding the HA polypeptide is at least 95%, at least 96%, at least 97%, at least 98% or at least 99% identical to nucleotides of 4-1698 of SEQ ID NO: 2 or nucleotides 4-1701 of SEQ ID NO: 4. In particular examples, the sequence of the nucleic acid molecule encoding the HA polypeptide comprises or consists of nucleotides of 4-1698 of SEQ ID NO: 2 or nucleotides 4-1701 of SEQ ID NO: 4.

In other embodiments, the sequence of the nucleic acid molecule encoding the HA polypeptide is at least 95%, at least 96%, at least 97%, at least 98% or at least 99% identical to nucleotides of 1-1698 of SEQ ID NO: 2 or nucleotides 1-1701 of SEQ ID NO: 4. In particular examples, the sequence of the nucleic acid molecule encoding the HA polypeptide comprises or consists of nucleotides of 1-1698 of SEQ ID NO: 2 or nucleotides 1-1701 of SEQ ID NO: 4.

In yet other embodiments, the sequence of the nucleic acid molecule encoding the HA polypeptide is at least 95%, at least 96%, at least 97%, at least 98% or at least 99% identical to SEQ ID NO: 2 or SEQ ID NO: 4. In particular examples, the sequence of the nucleic acid molecule comprises or consists of SEQ ID NO: 2 or SEQ ID NO: 4.

Vectors comprising the nucleic acid molecules encoding recombinant HA polypeptides are also provided by the present disclosure. The vector can be any suitable vector for expression of the HA polypeptide, such as a mammalian expression vector. In particular examples, the vector is the pTR600 expression vector (U.S. Patent Application Publication No. 2002/0106798, herein incorporated by reference; Ross et al., *Nat Immunol.* 1(2):102-103, 2000; Green et al., *Vaccine* 20:242-248, 2001).

In some examples, the vector includes a promoter operably linked to the nucleic acid sequence encoding the HA polypeptide. In particular examples, the promoter is a CMV promoter.

Also provided are isolated cells comprising the disclosed vectors. In some cases, the cell is any suitable cell type for production and expression of VLPs, such as a mammalian cell.

Further provided are influenza VLPs comprising an optimized HA polypeptide disclosed herein. The influenza VLPs can further include any additional influenza proteins necessary to form the virus particle. In some embodiments, the influenza VLPs further include influenza neuraminidase (NA) protein, influenza matrix (M1) protein, or both.

Also provided are influenza VLPs comprising an influenza HA polypeptide disclosed herein, produced by transfecting a host cell with a vector encoding the HA polypeptide, a vector encoding an influenza NA protein and a vector encoding an influenza M1 protein under conditions sufficient to allow for expression of the HA, M1 and NA proteins.

Fusion proteins comprising an optimized influenza HA polypeptide are further provided by the present disclosure.

Also provided herein are compositions comprising an optimized influenza HA protein as disclosed herein, or a fusion protein or VLP comprising the optimized influenza HA protein. In some embodiments, the compositions further comprise a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Further provided is a method of eliciting an immune response to influenza virus in a subject by administering an optimized influenza HA protein, a fusion protein comprising an optimized influenza HA, VLPs containing an optimized influenza HA, or compositions thereof, as disclosed herein. In some embodiments, the influenza virus is an H5N1 influenza virus. In some embodiments, the HA protein, HA fusion protein or VLP can be administered using any suitable route of administration, such as, for example, intramuscular, intranasal or oral. In some embodiments, the HA protein, fusion protein or VLP is administered as a composition further comprising a pharmaceutically acceptable carrier and/or an adjuvant. For example, the adjuvant can be alum, Freund's complete adjuvant, a biological adjuvant or immunostimulatory oligonucleotides (such as CpG oligonucleotides).

Also provided is a method of immunizing a subject against influenza virus by administering to the subject VLPs containing an optimized influenza HA protein disclosed herein, or administering a composition thereof. In some embodiments of the method, the composition further comprises a pharmaceutically acceptable carrier and/or an adjuvant. For example, the adjuvant can be alum, Freund's complete adjuvant, a biological adjuvant or immunostimulatory oligonucleotides (such as CpG oligonucleotides). In some embodiments, the VLPs (or compositions thereof) are administered intramuscularly.

In some embodiments of the methods of eliciting an immune response or immunizing a subject, the subject is administered about 1 to about 25 µg of the VLPs containing an optimized HA protein. In particular examples, the subject is administered about 5 to about 20 µg of the VLPs, or about 10 to about 15 µg of the VLPs. In one specific non-limiting example, the subject is administered about 15 µg of the VLPs. However, one of skill in the art is capable of determining a therapeutically effective amount (for example an amount that provides protection against H5N1 influenza virus infection) of VLPs to administer to a subject.

IV. Influenza

Influenza viruses are segmented negative-strand RNA viruses that belong to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Currently, sixteen subtypes of HA (H1-H16) and nine NA (N1-N9) antigenic variants are known for influenza A virus. Previously, only three subtypes were known to circulate in humans (H1N1, H1N2, and H3N2). However, in recent years, the pathogenic H5N1 subtype of avian influenza A has been reported to cross the species barrier and infect humans as documented in Hong Kong in 1997 and 2003, leading to the death of several patients.

In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2) (Krug et al., In "The Influenza Viruses," R. M. Krug, ed., Plenum Press, N.Y., 1989, pp. 89 152).

Influenza virus' ability to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

HA is a viral surface glycoprotein generally comprising approximately 560 amino acids and representing 25% of the total virus protein. It is responsible for adhesion of the viral particle to, and its penetration into, a host cell in the early stages of infection. Cleavage of the virus HA0 precursor into the HA1 and HA2 sub-fragments is a necessary step in order for the virus to infect a cell. Thus, cleavage is required in order to convert new virus particles in a host cell into virions capable of infecting new cells. Cleavage is known to occur during transport of the integral HA0 membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA1 and the carboxy terminal HA2. One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between virus and target cell membrane. This process is followed by fusion of the two membranes and entry of the virus into the target cell.

Proteolytic activation of HA involves cleavage at an arginine residue by a trypsin-like endoprotease, which is often an intracellular enzyme that is calcium dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acids in length, and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (Horimoto et al., *Clin Microbiol Rev.* 14(1):129-149, 2001).

In order to be packaged into progeny virions, viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., *J Virol,* 82:2295-2304, 2008). The M1 protein that lies within the envelope is thought to function in assembly and budding. A limited number of M2 proteins are integrated into the virions (Zebedee, *J. Virol.* 62:2762-2772, 1988). They form tetramers having H+ ion channel activity, and when activated by the low pH in endosomes, acidify the inside of the virion, facilitating its uncoating (Pinto et al., *Cell* 69:517-528, 1992). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable although it grew less efficiently than the parent virus in interferon-nondefective cells (Garcia-Sastre, *Virology* 252:324-330, 1998).

NS2 has been detected in virus particles (Richardson et al., *Arch. Virol.* 116:69-80, 1991; Yasuda et al., *Virology* 196:249-255, 1993). The average number of NS2 proteins in a virus particle was estimated to be 130-200 molecules. An in vitro binding assay shows direct protein-protein contact between M1 and NS2. NS2-M1 complexes have also been detected by immunoprecipitation in virus-infected cell lysates. The NS2 protein is thought to play a role in the export of RNP from the nucleus through interaction with M1 protein (Ward et al., *Arch. Virol.* 140:2067-2073, 1995).

V. Influenza VLPs and Administration Thereof

Influenza VLPs comprising an optimized HA (such as the HA having the amino acid sequence set forth as SEQ ID NO: 1 or SEQ ID NO: 3) are provided herein. The influenza VLPs are generally made up of the HA, NA and M1 proteins. The production of influenza VLPs has been described in the art and is within the abilities of one of ordinary skill in the art. For example, influenza VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. Example 3 below provides an exemplary protocol for purifying influenza VLPs from cell supernatants. In this example, VLPs are isolated by low speed centrifugation (to remove cell debris), vacuum filtration and ultracentrifugation through 20% glycerol.

The influenza VLPs disclosed herein can be used as influenza vaccines to elicit a protective immune response against human and avian H5N1 influenza viruses.

Influenza VLPs, or compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Influenza VLPs, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent H5N1 influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

Provided herein are pharmaceutical compositions which include a therapeutically effective amount of the influenza VLPs alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The influenza VLPs described herein can be administered alone or in combination with other therapeutic agents to enhance antigenicity. For example, the influenza VLPs can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcystein-lyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

Although administration of VLPs containing an optimized HA protein is exemplified herein, one of skill in the art would understand that it is also possible to administer the optimized influenza HA protein itself (in the absence of a viral particle) or as a fusion protein to elicit an immune response in a subject. In some embodiments, a fragment of the HA protein is administered such as the HA1 or HA2 sub-fragment.

The following examples are provided to illustrate certain particular features and/or embodiments. These examples should not be construed to limit the disclosure to the particular features or embodiments described.

EXAMPLES

Example 1: Generation of a H5N1 Influenza COBRA Sequence

This example describes the generation of a H5N1 influenza HA COBRA consensus sequence using 1,989 human and avian H5N1 influenza HA sequences. The resultant COBRA sequence is referred to as "All H5 COBRA."

To generate the final H5N1 influenza HA COBRA sequence, three layers of consensus sequences were used (FIG. 1). For the first layer, a consensus sequence was generated for each H5N1 clade and subclade (clades 0, 1, 2.1.1, 2.1.2, 2.1.3, 2.2, 2.3.1, 2.3.2, 2.3.3, 2.3.4, 2.4, 2.5, 3, 4, 5, 6, 7, 8 and 9). The second layer included a consensus sequences for each of the five subclades of clade 2 (2.1, 2.2, 2.3, 2.4 and 2.5). For the third layer, a final consensus sequence was generated using the consensus sequences of each of the 10 clades (0, 1, 2, 3, 4, 5, 6, 7, 8 and 9). The H5N1 COBRA sequence generated according to this method is shown below and is set forth herein as SEQ ID NO: 1.

All H5 COBRA HA
(SEQ ID NO: 1)
MEKIVLLLAIVSLVKSDQICIGYHANNSTEQVDTIMEKNVTVTHAQDILE

KTHNGKLCDLDGVKPLILRDCSVAGWLLGNPMCDEFINVPEWSYIVEKAS

PANDLCYPGDFNDYEELKHLLSRINHFEKIQIIPKSSWSNHEASSGVSSA

CPYQGKSSFFRNVVWLIKKNSAYPTIKRSYNNTNQEDLLVLWGIHHPNDA

AEQTKLYQNPTTYISVGTSTLNQRLVPKIATRSKVNGQSGRMEFFWTILK

PNDAINFESNGNFIAPEYAYKIVKKGDSAIMKSELEYGNCNTKCQTPMGA

INSSMPFHNIHPLTIGECPKYVKSNRLVLATGLRNSPQRERRRKKRGLFG

AIAGFIEGGWQGMVDGWYGYHHSNEQGSGYAADKESTQKAIDGVTNKVNS

IIDKMNTQFEAVGREFNNLERRIENLNKKMEDGFLDVWTYNAELLVLMEN

ERTLDFHDSNVKNLYDKVRLQLRDNAKELGNGCFEFYHKCDNECMESVRN

GTYDYPQYSEEARLKREEISGVKLESIGTYQILSIYSTVASSLALAIMVA

GLSLWMCSNGSLQCRI

The final COBRA amino acid sequence was reverse translated and optimized for expression in mammalian cells, including codon usage and RNA optimization (GeneArt; Regensburg, Germany). The codon optimized gene sequence is provided below and is set forth herein as SEQ ID NO: 2.

Codon-optimized All H5 COBRA HA gene sequence
(SEQ ID NO: 2)
atggaaaagatcgtgctgctgctggccatcgtgtccctggtgaagagcga ccagatttgcattggctaccacgccaacaatagcacagagcaggtggaca ccatcatggagaaaaacgtgaccgtgacccacgcccaggacatcctggag aaaacccacaacggcaagctgtgtgacctggacggcgtgaagcccctgat cctgagagactgctccgtggccggctggctgctgggcaaccccatgtgtg acgagttcatcaacgtgcccgagtggagctacatcgtggagaaggccagc cccgccaacgacctgtgctaccccggcgacttcaacgactacgaggagct gaagcacctgctgtcccggatcaaccacttcgagaagatccagatcatcc ccaagagcagctggagcaaccacgaggccagcagcggcgtgtccagcgcc tgccctaccagggcaagagcagcttcttccggaacgtggtctggctgat caagaagaactctgcctatcccaccatcaagcggagctacaacaacacca accaggaggatctgctggtcctgtggggcatccaccaccccaacgacgcc gccgagcagaccaagctgtaccagaaccccaccacctacatcagcgtggg caccagcaccctgaaccagcggctggtgcccaagatcgccacccggtcca aagtgaacggccagagcggccggatggaattcttctggaccatcctgaag cccaacgatgccatcaacttcgagagcaacggcaacttcatcgcccccga gtacgcctacaagatcgtgaagaagggcgacagcgccatcatgaagagcg agctggaatacggcaactgcaacaccaagtgccagacccccatgggcgcc atcaacagcagcatgcccttccacaacatccacccccctgaccatcggcga gtgccccaagtacgtgaagagcaacaggctggtgctggccaccggcctgc ggaacagccccagcgggagcggcggaggaagaagcggggcctgttcggc gccatcgccggcttcatcgagggcggctggcagggcatggtggacgggtg gtacggctaccaccacagcaatgagcagggcagcggctacgccgccgaca aagagagcacccagaaggccatcgacggcgtcaccaacaaggtgaacagc atcatcgacaagatgaacacccagttcgaggccgtgggccgggagttcaa caacctggaacggcggatcgagaacctgaacaagaaaatggaagatggct tcctggacgtgtggacctacaacgccgaactcctggtgctgatggaaaac gagcggaccctggacttccacgacagcaacgtgaagaacctgtacgacaa agtgcggctgcagctgcgggacaacgccaaagagctgggcaacggctgct tcgagttctaccacaagtgcgacaacgagtgcatggaaagcgtgcggaac ggcacctacgactaccccccagtacagcgaggaagcccggctgaagcggga ggaaatcagcggcgtgaaactggaaagcatcggcacctaccagatcctga gcatctacagcaccgtggccagcagcctcgctctggccattatggtggcc ggcctgagcctgtggatgtgcagcaacggcagcctgcagtgccggatcgg atccagatctgctagcgtcgactctagattaattaa The codon-optimized construct can be inserted into the pTR600 expression vector (U.S. Patent Application Publication No. 2002/0106798; Ross et al., *Nat Immunol.* 1(2): 102-103, 2000; Green et al., *Vaccine* 20:242-248, 2001) and used for the production of VLPs, as discussed below in Example 3.

Example 2: Generation of a Human/Avian Clade 2 H5N1 COBRA Sequence

This example describes the generation of a H5N1 influenza HA COBRA consensus sequence using 1213 human and avian H5N1 clade 2 influenza HA sequences. The resultant COBRA sequence is referred to as "Human-Avian COBRA-2."

To generate the final human/avian influenza HA COBRA sequence, two layers of consensus sequences were used (FIG. 2). For the first layer, five consensus sequences were generated using sequences from 10 subclades of H5N1 clade 2 (subclades 2.1.1, 2.1.2, 2.1.3, 2.2, 2.3.1, 2.3.2, 2.3.3, 2.3.4, 2.4 and 2.5). For the second layer, a final consensus sequence was generated using the five consensus sequences (clade 2.1, clade 2.2, clade 2.3, clade 2.4 and clade 2.5) generated in the first layer. The human/avian H5N1 clade 2 COBRA sequence generated according to this method is shown below and is set forth herein as SEQ ID NO: 3.

Human-Avian COBRA-2 HA
(SEQ ID NO: 3)
MEKIVLLLAIVSLVKSDQICIGYHANNSTEQVDTIMEKNVTVTHAQDILE

KTHNGKLCDLDGVKPLILRDCSVAGWLLGNPMCDEFINVPEWSYIVEKAN

PANDLCYPGNFNDYEELKHLLSRINHFEKIQIIPKSSWSDHEASSGVSSA

CPYQGKSSFFRNVVWLIKKNSAYPTIKRSYNNTNQEDLLVLWGIHHPNDA

AEQTRLYQNPTTYISVGTSTLNQRLVPKIATRSKVNGQSGRMEFFWTILK

PNDAINFESNGNFIAPEYAYKIVKKGDSAIMKSELEYGNCNTKCQTPMGA

-continued
INSSMPFHNIHPLTIGECPKYVKSNRLVLATGLRNSPQRERRRKRGLFGA

IAGFIEGGWQGMVDGWYGYHHSNEQGSGYAADKESTQKAIDGVTNKVNSI

IDKMNTQFEAVGREFNNLERRIENLNKKMEDGFLDVWTYNAELLVLMENE

RTLDFHDSNVKNLYDKVRLQLRDNAKELGNGCFEFYHKCDNECMESVRNG

TYDYPQYSEEARLKREEISGVKLESIGTYQILSIYSTVASSLALAIMVAG

LSLWMCSNGSLQCRICI

The final COBRA amino acid sequence was reverse translated and optimized for expression in mammalian cells, including codon usage and RNA optimization (GeneArt; Regensburg, Germany). The codon optimized gene sequence is provided below and is set forth herein as SEQ ID NO: 4.

```
Codon-optimized Human-Avian COBRA-2 HA gene
sequence
                                        (SEQ ID NO: 4)
atggagaagatcgtgctgctgctggccatcgtgtccctggtgaagagcga ccagatttgcatcggctaccacgccaacaatagcaccgagcaagtggaca ccatcatggagaaaacgtgaccgtgacccacgctcaggacatcctcgaa aaacccacaacggcaagctgtgcgatctggacggcgtgaagcccctgat cctgagagactgcagcgtggccggctggctgctgggcaatcccatgtgcg acgagttcatcaacgtgcccgagtggagctacatcgtggagaaggccaac cccgccaacgacctgtgctaccccggcaacttcaacgactacgaggagct gaagcacctgctgagccggatcaaccacttcgagaagatccagatcatcc ccaagagcagctggagcgaccatgaggcaagcagcggcgtgtccagcgcc tgcccctaccagggcaagtccagcttcttccgcaacgttgtgtggctgat caagaagaacagcgcctaccccaccatcaagcggagctacaacaacacca accaggaggacctgctggtcctgtggggcatccaccacccaacgacgcc gccgagcagaccggctgtaccagaacccaccacctacatctctgtggg caccagcaccctgaaccagcggctggtgcccaagatcgccacccggagca aggtgaacgccagagcggccggatggagttcttctggaccatcctgaag cccaacgatgccatcaacttcgagagcaacggcaacttcatcgcccccga gtacgcctacaagatcgtgaagaagggcgacagcgccatcatgaagtccg agctggagtacggcaactgtaacaccaagtgccagaccccatgggcgcc atcaacagcagcatgcccttccacaacatccaccccctgaccatcggcga gtgccccaagtacgtgaagagcaacaggctggtgctggccaccggcctga gaaacagcccccagagagagcggagaagaaagagaggcctgttcggcgcc attgccggcttcatcgagggcggctggcagggcatggtggacgggtggta cggctaccaccactccaacgagcagggcagcggctacgccgccgacaaag agagcacccagaaagctatcgacggcgtgaccaacaaagtgaacagcatc atcgacaagatgaatacccagttcgaggccgtgggcagagagttcaacaa cctggaaagaagaatcgagaacctgaacaagaaaatggaagatggctttc tggatgtgtggacctacaacgccgagctgctggtgctgatggaaaacgag cggaccctggacttccacgacagcaacgtgaagaatctgtacgacaaagt
```

-continued
```
gcggctgcagctgagagacaacgccaaagagctgggcaacggctgcttcg agttctaccacaagtgcgacaatgagtgcatggaaagcgtgcggaacggc acctacgactacccccagtacagcgaggaagcccggctgaagagagaaga gatttccggcgtgaagctggaaagcatcggcacctaccagatcctgagca tctacagcaccgtggccagcagcctggccctggccatcatggtggccggc ctgagcctgtggatgtgcagcaacggcagcctgcagtgccggatctgcat cggatccagatctgctagcgtcgactctagattaattaa
```

The codon-optimized construct can be inserted into the pTR600 expression vector (U.S. Patent Application Publication No. 2002/0106798; Ross et al., *Nat Immunol.* 1(2): 102-103, 2000; Green et al., *Vaccine* 20:242-248, 2001) and used for the production of VLPs, as discussed below in Example 3.

Example 3: Preparation of and Immunization with Influenza VLPs

The following methods can be used to produce and characterize influenza VLPs comprising a COBRA HA. Exemplary methods for immunization of mice, ferrets and macaques are also described below (see also, Giles and Ross, *Vaccine* 29(16):3043-3054, 2011).

Vaccine Preparation 293T cells are transiently transfected with plasmids expressing M1, NA and an optimized HA, and incubated for 72 hours at 37° C. The M1, NA and HA coding sequences can be codon-optimized for expression in mammalian cells. Supernatants are collected and cell debris is removed by low speed centrifugation followed by vacuum filtration through a 0.22 μm sterile filter. VLPs are purified via ultracentrifugation (100,000×g through 20% glycerol, weight per volume) for 4 hours at 4° C. The pellets are subsequently resuspended in PBS pH 7.2 and stored in single use aliquots at −80° C. until use. Total protein concentration is determined by Micro BCA™ Protein Assay Reagent Kit (Pierce Biotechnology, Rockford, Ill., USA).

Dose Determination

HA specific content can be determined by western blot and densitometry. Purified recombinant COBRA HA and purified VLPs are prepared in standard total protein amounts and are electrophoresed on a 10% SDS-PAGE gel and transferred to a PVDF membrane. The blot is probed with mouse polyclonal antisera from influenza infected mice and the HA-antibody complexes are detected using a goat anti-mouse IgG conjugated to horseradish peroxidase (HRP) (Southern Biotech; Birmingham, Ala., USA). HRP is detected by chemiluminescent substrate (Pierce Biotechnology; Rockford Ill., USA) and exposed to X-ray film (ThermoFisher; Pittsburgh, Pa., USA). Density of bands is determined using ImageJ software (NIH). Density of recombinant HA bands is used to calculate a standard curve and the density of the purified VLPs is interpolated using the results from the recombinant HA.

Mouse Studies

BALB/c mice (*Mus musculis*, females, 6-8 weeks old) can be purchased from Harlan Sprague Dawley (Indianapolis, Ind., USA). Mice are housed in microisolator units and allowed free access to food and water and are cared for under USDA guidelines for laboratory animals. Mice are vaccinated with a selected dose of purified COBRA HA VLPs (such as a dose of 3.0 μg, 1.5 μg, 0.6 μg, 0.3 μg or 0.06 μg), based upon HA content from a densitometry assay, via intramuscular injection at week 0 and then boosted with the same dose at week 3. Vaccines at each dose are formulated with alum adjuvant (Imject Alum, Pierce Biotechnology; Rockford, Ill., USA), CpG oligonucleotides, or vehicle alone. Fourteen to twenty-one days after each vaccination, blood is collected from anesthetized mice via the retro-orbital plexus and transferred to a microfuge tube. Tubes are centrifuged and sera is removed and frozen at −80±5° C. Hemagglutination inhibition (HAI) serum antibody titer for each vaccine group is determined at week 5 using representative reassortant viruses or COBRA HA VLPs.

Three weeks after final vaccination, mice are challenged intranasally with a pathogenic H5N1 influenza virus in a volume of 50 μl. After infection, mice are monitored daily for weight loss, disease signs and death for 14 days after infection. Individual body weights, sickness scores (Toapanta and Ross, *Respiratory Research* 10(1):112, 2009) and death are recorded for each group on each day after inoculation.

Ferret Studies

Fitch ferrets (*Mustela putorius furo*, female, 6-12-months of age), influenza naïve and de-scented, can be purchased from Marshall Farms (Sayre, Pa., USA). Ferrets are pair housed in stainless steel cages (Shor-line, Kansas City, Kans., USA) containing Sani-chips Laboratory Animal Bedding (P.J. Murphy Forest Products, Montville, N.J., USA). Ferrets are provided with Teklad Global Ferret Diet (Harlan Teklad, Madison, Wis., USA) and fresh water ad libitum. The COBRA HA VLPs are diluted in PBS, pH 7.2 to achieve final concentration. Ferrets are vaccinated with one of two doses of purified COBRA VLPs (15 μg, 3 μg), based upon HA content as determined by densitometry assay, via intramuscular injection in the quadriceps muscle in a volume of 0.25 ml at week 0 and then boosted with the same dose at week 3. Vaccines are stored at −80° C. prior to use and formulated with alum adjuvant (Imject Alum; Pierce Biotechnology, Rockford, Ill., USA) immediately prior to use. Animals are monitored for adverse events including weight loss, temperature, decrease in activity, nasal discharge, sneezing and diarrhea weekly during the vaccination regimen. Prior to vaccination, animals are confirmed by HAI assay to be seronegative for circulating influenza A and influenza B viruses. Fourteen to twenty-one days after each vaccination, blood is collected from anesthetized ferrets via the anterior vena cava and transferred to a microfuge tube. Tubes are centrifuged and sera is removed and frozen at −80±5° C. HAI serum antibody titer for each vaccine group is determined at week 5 using representative reassortant viruses or COBRA HA VLPs.

Three weeks after final vaccination, ferrets are challenged intranasally with a pathogenic H5N1 influenza virus in a volume of 1 ml. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at −80° C. until use.

Primate Immunizations

Cynomolgus macaques (*Macaca fascicularis*, male, 3-5 years old) can be purchased from Harlan Sprague Dawley (Indianapolis, Ind., USA). Macaques are vaccinated with purified COBRA HA VLPs (15 μg), based upon HA content from a densitometry assay, via intramuscular injection at week 0 and then boosted with the same dose at weeks 3 and 6. Vaccines are formulated with alum adjuvant (Imject Alum, Pierce Biotechnology; Rockford, Ill., USA) immediately prior to use. Twenty-one days after each vaccination, blood is collected from anesthetized macaques via the femoral vein and transferred to a serum separator tube. Tubes are allowed to activate clotting followed by centrifugation and sera is removed and frozen at −80±5° C. End point IgG titers and HAI serum antibody titer for each vaccine group is determined at week 5 using representative reassortant viruses or COBRA HA VLPs.

Three weeks after final vaccination, macaques are challenged by intranasal, intratracheal, and orbital inoculation with a pathogenic H5N1 influenza virus in a volume of 1 ml. After infection, macaques are monitored daily for weight loss, disease signs and death for 5 days after infection. Individual body weights, sickness scores and death are recorded for each group on each day after inoculation.

Example 4: Immunogenicity and Protective Efficacy of COBRA HA-Containing VLPs

This example describes five studies in mice to test the immunogenicity and protective efficacy of All H5 COBRA VLPs and Human-Avian COBRA-2 VLPs.

COBRA Study 1A

This study was conducted to test the immunogenicity of All H5 COBRA and Human-Avian COBRA-2, and protective efficacy against clade 1 and clade 2 challenges. VLPs containing a human clade 2 COBRA HA (Human COBRA-2 VLPs) were used for comparison. Mice were vaccinated intramuscularly with 3 μg of VLPs containing the All H5 COBRA HA sequence (SEQ ID NO: 1), VLPs containing the Human-Avian COBRA-2 HA sequence (SEQ ID NO: 3), VLPs containing the Human COBRA-2 HA sequence, or VLPs containing Whooper Swan (A/Whooper Swan/Mongolia/244/2005) influenza virus HA. Vaccinations were performed at week 0 and week 3 with an adjuvant (Imject™). Mice were challenged with 5000 PFU of Indonesia clade 2.1 virus (A/Indonesia/5/2005) or 5000 PFU of Vietnam clade 1 virus (A/Vietnam/1203/2004) during week 5. Blood samples were collected at week 3 and week 5. Lungs were harvested at day 3 (D3) after challenge for viral titers.

Figure 4:
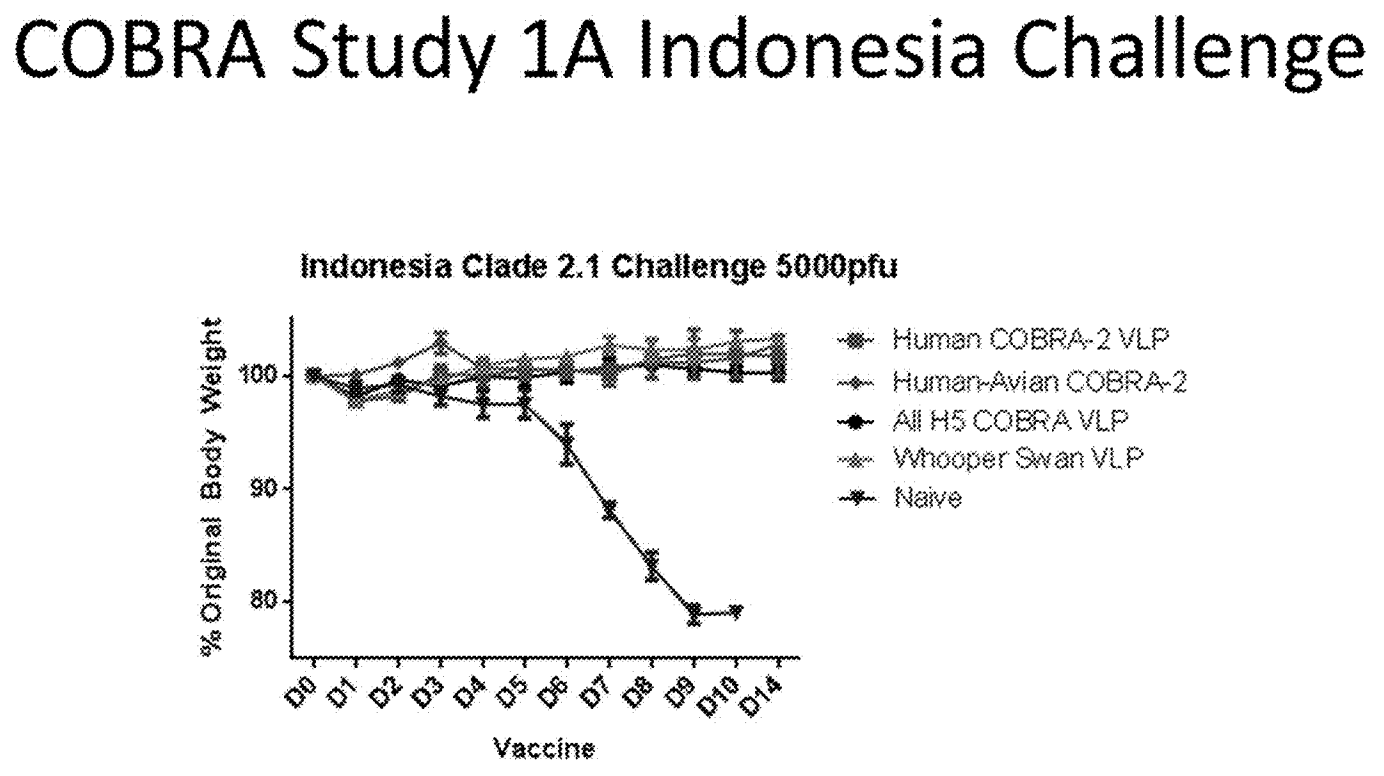

HAI titers against All H5 COBRA VLPs (positive control), Vietnam clade 1 virus, Indonesia clade 2.1.3 virus, Whooper Swan clade 2.2 virus, Turkey clade 2.2 virus (Tk/Tk/05), two Egypt clade 2.2.1 viruses (Eg/321/07 and Eg/3300/08), Anhui clade 2.3.4 virus (Anhui/1/2005), Japanese white eye clade 2.3.4 virus (JWE/1038/06) and chicken Vietnam clade 7 virus (Ck/VN/08) in vaccinated mice are shown in FIG. 3. The results demonstrate that vaccination with All H5 COBRA and Human-Avian COBRA-2 HA-containing VLPs elicits an antibody response that can recognize both clade 1 and clade 2 influenza viruses. Body weights of vaccinated and naïve mice up to day 14 (D14) post-challenge with Indonesia clade 2.1 and with Vietnam clade 1 are shown in FIG. 4 and FIG. 5, respectively. All vaccinated mice showed very little change in body weight over time, whereas naïve mice exhibited a significant weight loss. In addition, viral titers in naïve mice following challenge with Whooper Swan clade 2.2 virus (FIG. 6) or Vietnam clade 1 virus (FIG. 7) were significantly greater than viral titers in vaccinated mice following challenge.

COBRA Study 2A

This study was conducted to test protective efficacy against clade 1 challenge following a single vaccination of mice with VLPs containing All H5 COBRA, Human-Avian COBRA-2, or Human COBRA-2 HA. Mice were vaccinated intramuscularly with 3 μg of All H5 COBRA VLPs, Human- Avian COBRA-2 VLPs, Human COBRA-2 VLPs, or Whooper Swan VLPs. Vaccination was performed with an adjuvant (Imject™). Mice were challenged with 5000 PFU of Vietnam clade 1 virus during week 4. Blood samples were collected at week 3. Lungs were harvested at day 2 (D2) and day 3 (D3) after challenge for viral titers.

As shown in FIG. 8, the body weight of vaccinated mice did not significantly change following challenge with Vietnam clade 1 virus, whereas naïve mice exhibited a significant loss in weight. Virus titers at D2 and D3 in naïve mice were also significantly greater compared with vaccinated mice (FIG. 9).

COBRA Study 4A

This study was conducted to test protective efficacy against clade 1 virus following a single vaccination in the absence of adjuvant. Mice were vaccinated intramuscularly with 3 µg of All H5 COBRA VLPs, Human-Avian COBRA-2 VLPs, Human COBRA-2 VLPs, or Whooper Swan VLPs. Mice were challenged with 5000 PFU of Vietnam clade 1 virus during week 4. Blood samples were collected at week 3. Lungs were harvested at D2 and D3 after challenge for viral titers.

As shown in FIG. 10, the body weight of all mice vaccinated without adjuvant dropped initially following clade 1 challenge, but returned to normal by D10 following challenge. In contrast, the weight of naïve mice dropped significantly and did not recover. Naïve mice succumbed to infection by day 7, whereas 40-60% of vaccinated mice survived challenge out to day 14 (FIG. 11). Specifically, 60% of mice vaccinated with All H5 COBRA VLPs or Human COBRA-2 VLPs survived challenge, and 40% of mice vaccinated with Human-Avian COBRA-2 or Whooper Swan VLPs survived challenge.

COBRA Study 5A

This study was conducted to test protective efficacy against clade 1 virus following a single vaccination with adjuvant (Imject™) at a lower dose of VLP (0.6 µg). Mice were vaccinated intramuscularly with 0.6 µg of All H5 COBRA VLPs, Human-Avian COBRA-2 VLPs, Human COBRA-2 VLPs, or Whooper Swan VLPs. Mice were challenged with 5000 PFU of Vietnam clade 1 virus during week 4. Blood samples were collected at week 3. Lungs were harvested at D2 and D3 after challenge for viral titers.

As shown in FIG. 12, body weight of vaccinated mice dropped slightly following virus challenge but returned to normal levels by D10. In contrast, body weight of naïve mice dropped significantly and the mice did not recover. Virus titers at D2 and D3 in naïve mice were also greater compared with vaccinated mice (FIG. 13 and FIG. 14).

COBRA Study 9A

This study was conducted to test protective efficacy against clade 2.2 virus following a single vaccination with adjuvant (Imject™) at a lower dose of VLP (0.6 µg). Mice were vaccinated intramuscularly with 0.6 µg of All H5 COBRA VLPs, Human-Avian COBRA-2 VLPs, Human COBRA-2 VLPs, or Whooper Swan VLPs. Mice were challenged with 5000 PFU of Whooper Swan clade 2.2 virus during week 4. Blood samples were collected at week 3. Lungs were harvested at D2 and D3 after challenge for viral titers.

As shown in FIG. 15, body weight of vaccinated mice dropped slightly following virus challenge but returned to normal levels by D10. In contrast, body weight of naïve mice dropped significantly and the mice did not recover. Virus titers at D2 and D3 in naïve mice were also increased relative to vaccinated mice (FIG. 16 and FIG. 17).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated nucleic acid molecule encoding a recombinant influenza hemagglutinin (HA) polypeptide, wherein the amino acid sequence of the polypeptide comprises an amino acid sequence at least 99.8% identical to residues 2-566 of SEQ ID NO: 1 or at least 99.6% identical to residues 2-567 of SEQ ID NO: 3.

2. The isolated nucleic acid molecule of claim 1, wherein the amino acid sequence of the polypeptide comprises an amino acid sequence at least 99.8% identical to SEQ ID NO: 1 or at least 99.6% identical to SEQ ID NO: 3.

3. The isolated nucleic acid molecule of claim 1, wherein the amino acid sequence of the polypeptide comprises no more than 1 amino acid substitution relative to SEQ ID NO: 1 or no more than 2 amino acid substitutions relative to SEQ ID NO: 3.

4. The isolated nucleic acid molecule of claim 1, wherein the amino acid sequence of the polypeptide comprises residues 2-566 of SEQ ID NO: 1 or residues 2-567 of SEQ ID NO: 3.

5. The isolated nucleic acid molecule of claim 1, wherein the amino acid sequence of the polypeptide consists of residues 2-566 of SEQ ID NO: 1 or residues 2-567 of SEQ ID NO: 3.

6. The isolated nucleic acid molecule of claim 2, wherein the amino acid sequence of the polypeptide comprises SEQ ID NO: 1 or SEQ ID NO: 3.

7. The isolated nucleic acid molecule of claim 2, wherein the amino acid sequence of the polypeptide consists of SEQ ID NO: 1 or SEQ ID NO: 3.

8. The isolated nucleic acid molecule of claim 1, wherein the nucleic acid molecule is codon-optimized for expression in mammalian cells.

9. The isolated nucleic acid molecule of claim 8, comprising nucleotides 4-1698 of SEQ ID NO: 2 or nucleotides 4-1701 of SEQ ID NO: 4.

10. The isolated nucleic acid molecule of claim 8, comprising nucleotides 1-1698 of SEQ ID NO: 2 or nucleotides 1-1701 of SEQ ID NO: 4.

11. The nucleic acid molecule of claim 8, comprising the nucleotide sequence of SEQ ID NO: 2 or SEQ ID NO: 4.

12. A vector comprising the nucleic acid molecule of claim 1.

13. The vector of claim 12, further comprising a promoter operably linked to the nucleic acid sequence encoding the influenza HA polypeptide.

14. An isolated cell comprising the vector of claim 12.

* * * * *